United States Patent [19]
Poon et al.

[11] Patent Number: 5,871,008
[45] Date of Patent: Feb. 16, 1999

[54] MINIATURE HIGH-FREQUENCY VENTILATOR

[75] Inventors: Chi-Sang Poon, Lexington; Kumaran Kolandaivelu, Boston, both of Mass.

[73] Assignee: Massachusetts Institute of Technology, Cambridge, Mass.

[21] Appl. No.: 725,414

[22] Filed: Oct. 3, 1996

Related U.S. Application Data

[60] Provisional application No. 60/005,035 Oct. 6, 1995.

[51] Int. Cl.$^6$ .................................................. A61G 10/00
[52] U.S. Cl. .................. 128/202.12; 601/44; 128/205.26
[58] Field of Search .................. 128/202.12, 205.26; 601/41, 43, 44

[56] References Cited

U.S. PATENT DOCUMENTS

| | | | |
|---|---|---|---|
| 4,620,538 | 11/1986 | Koegel et al. | 601/43 |
| 4,621,621 | 11/1986 | Marsalis | 128/202.12 |
| 4,770,165 | 9/1988 | Hayek | 128/202.12 |
| 4,815,452 | 3/1989 | Hayek | 601/44 |
| 4,838,263 | 6/1989 | Warwick et al. | 601/44 |
| 4,840,167 | 6/1989 | Olsson et al. | 601/44 |
| 4,930,498 | 6/1990 | Hayek | 601/44 |
| 4,977,889 | 12/1990 | Budd | 601/44 |
| 4,982,735 | 1/1991 | Yagata et al. | 601/44 |
| 5,056,505 | 10/1991 | Warwick et al. | 601/44 |

OTHER PUBLICATIONS

Harf et al., Journal of Applied Physiology, "Ventilation by high–frequency oscillation of thorax or at trachea in rats", vol. 56, No. 1, pp. 155–160, 1984.

Kolandaivelu et al., Journal of Applied Physiology, A miniature mechanical ventilator for newborn mice, vol. 84, No. 2, 1998.

Stern et al., Canadian Medical Association Journal, "Negative presure artifical respiration: use in treatment of respiratory failure of the newborn", vol. 102, No. 6, pp. 595–601, Mar. 28, 1970.

Linsao et al., Canadian Medical Association Journal, "Negative presure artifical respiration: use in treatment of respiratory distress syndrome of the newborn", vol. 102, No. 6, pp. 602–606, Mar. 28, 1970.

*Primary Examiner*—Aaron J. Lewis
*Attorney, Agent, or Firm*—Samuels, Gauthier, Stevens & Reppert

[57] ABSTRACT

A high-frequency miniature pressure ventilator system including a variable volume pressure chamber arranged to surround a portion of the thoracic cavity of a body so as to isolate the portion of the body from atmospheric pressure. A pump assembly is operable for varying the pressure within the chamber so as to apply negative external pressure to the portion of the body during a negative cycle of operation. A valve assembly is operable for opening the chamber to a predetermined pressure during a positive cycle of operation in order to normalize a base pressure from which the pressure within said chamber is varied. In another embodiment there is provided a high-frequency pressure ventilator system including a variable volume pressure chamber arranged to surround the head of a body so as to isolate the head from atmospheric pressure. A pump assembly is operable for varying the pressure within the chamber so as to apply positive external pressure to the head during a positive cycle of operation. A valve assembly is operable for opening the chamber to predetermined pressure during a negative cycle of operation in order to normalize a base pressure from which the pressure within said chamber is varied.

22 Claims, 15 Drawing Sheets

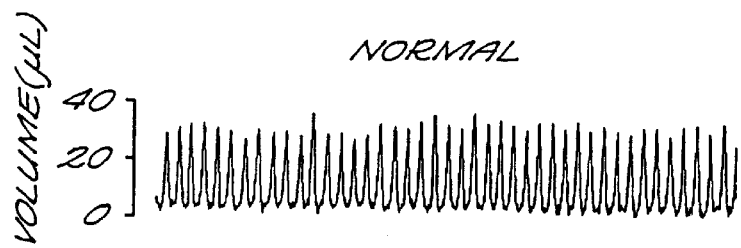
FIG. 1A
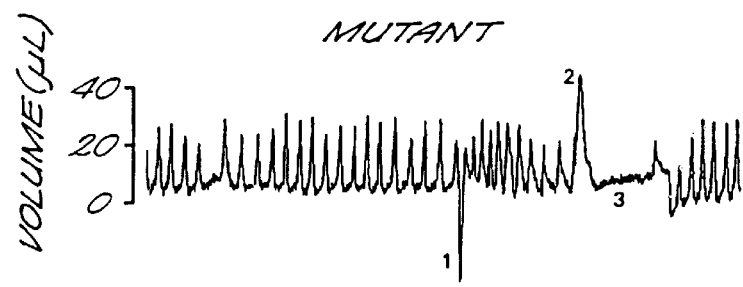
FIG. 1B
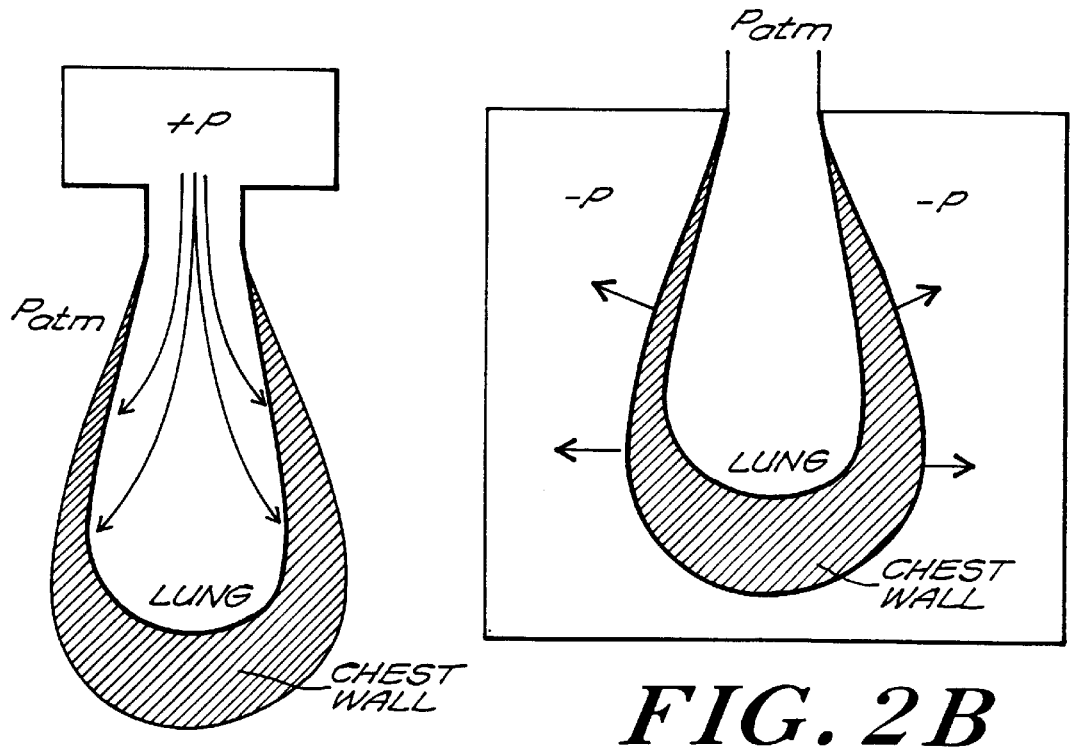
FIG. 2A
FIG. 2B

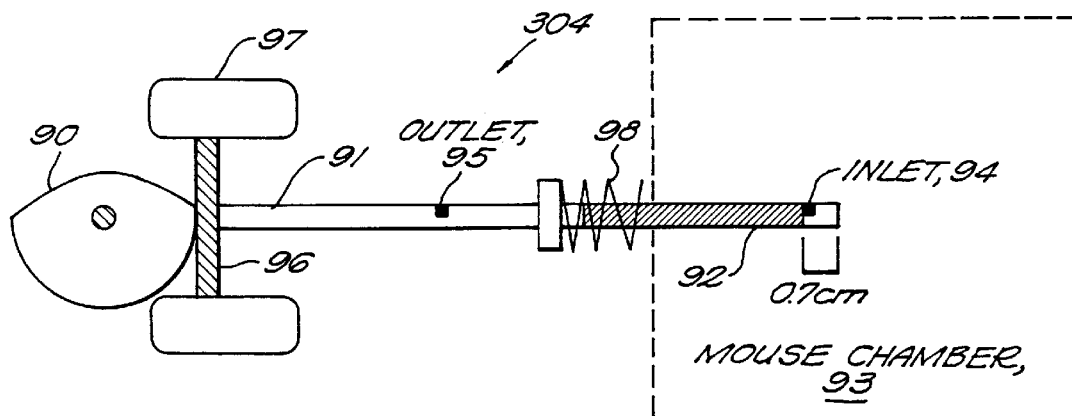
FIG. 9B
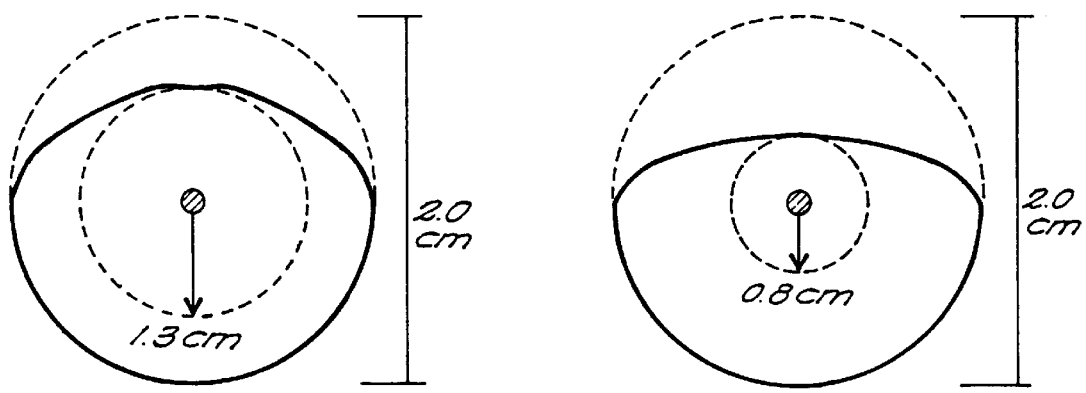
FIG. 10A   FIG. 10B
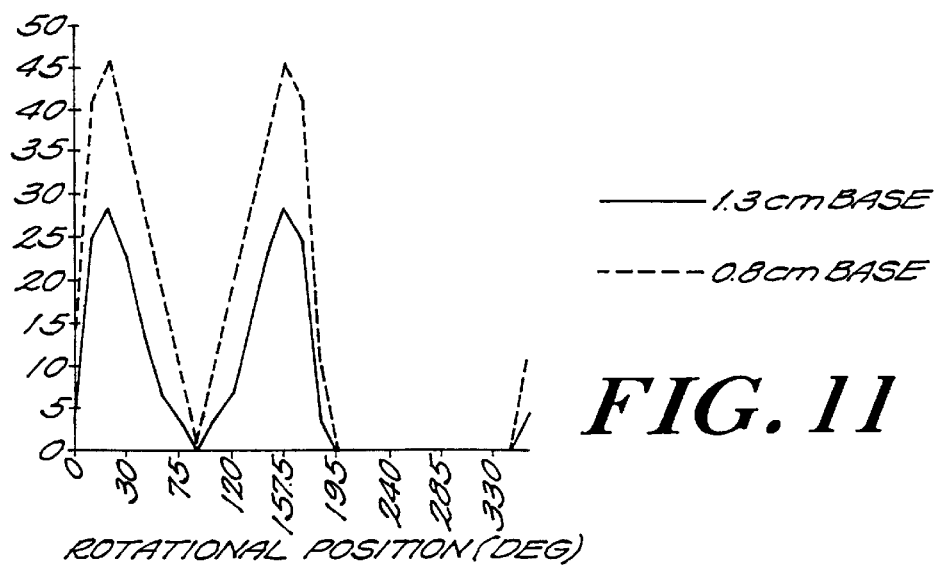
FIG. 11

MINIATURE HIGH-FREQUENCY VENTILATOR

This invention was made with government support under grant number NIH-5R01-HL45261 awarded by the National Institutes of Health. The government has certain rights in the invention.

This application claims priority to provisional application Ser. No. 60/005,035 filed on Oct. 6, 1995.

BACKGROUND OF THE INVENTION

The invention relates to a miniature high-frequency ventilator for small animals or human infants.

Genetically engineered mice, made possible by techniques of molecular biology, are a valuable resource in furthering both the medical and biological sciences. By changing the chromosomal content in specific ways, various proteins can be knocked out or altered, whose expression or lack thereof can be investigated. The mice are a choice animal for such studies. Presently, much of their genome has been mapped. Additionally, like humans, they are mammals and therefore share many homologous chromosomes. By studying mice, further insight into human function can be gained. Furthermore, the mice can be bred with regularity and ease.

Unfortunately, the physical expression of mutations can sometimes be detrimental to the well-being of the mice. Various problems such as cardiac or respiratory failure can occur, causing premature death. Presently, there is no equipment designed to sustain newborn animals of this size, and such problems go unsolved.

The need for a miniature mechanical ventilator for newborn mice has arisen from recent studies on NMDA-R1 genetically engineered mice. The NMDA-R1 molecule is a key component of NMDA receptors. These receptors are believed to play a critical role in the plasticity of the nervous system. Unfortunately, the mice die within the first 10 to 20 hours after birth—prior to most major neurological developments—precluding further studies into the role of NMDA receptors in learning and memory.

The recessive mutation has various side effects. Some studied abnormalities include loss of hind leg motor control and balance, improper mastication (leading to an inability to suckle milk), and a degradation of the respiratory system. Observation of these symptoms has proven to be an effective determinant of the genetic make up (either homozygous recessive, or homozygous/heterozygous dominant) when compared to genetic prototyping data.

Previous studies have shown that the respiratory failure is preceded by periods of apnea and respiratory instability. FIGS. 1A and 1B respectively show graphical representations of breathing samples for normal and mutant newborn mice. One hypothesis that has been raised is that the early deaths of the newborn mutants are caused by this failure.

By artificially ventilating the "knockout" mice, the respiratory system may be preserved, prolonging the lives of the mice for a more thorough study into the roles of the NMDA receptors in neuroplasticity and neural development.

Current animal ventilators are not suitable to ventilate neonatal mice. They are designed to deliver positive pressure at the airways via pistons, diaphragms, or pressure sources. Being designed for larger animals, the devices generally deliver volumes of at least a few milliliters. Previous studies have shown that the newborn mice have tidal volumes ranging from 0.015 to 0.045 ml. Existing devices would therefore be imprecise over the required range. Such unreliability could result in uncontrolled volume generation and barotrauma for the fragile newborns.

A further problem with the current ventilators is that creating a positive pressure at the airway generally requires an intratracheal connection. Though this surgical procedure can be performed with some confidence in larger animals, a tracheotomy is too difficult to perform on newborn mice. Generally, this technique requires opening the throat and inserting a tube into the thrachea, an extremely invasive operation considering the size and fragility of the neonates. Such trauma makes the use of this ventilatory style an impossibility in the mutant mice.

A final concern with current methods of animal mechanical respiration is that the ventilators deliver automatic breaths at regular intervals. Such mechanically controlled breathing creates a problem, especially since the knockout mice breathe over a wide range of frequencies. The normal frequency is about 120 breaths per minute (bpm). However, depending on the stage of respiratory distress, much lower frequencies are observed (60 bpm). Delivering automatic breaths at a significantly different frequency than the spontaneous rate can be uncomfortable, and moreover, generate ventilator fighting. This condition arises when some of the animal breaths are out of phase with the mechanical breaths (i.e. the animal expires while the ventilator gives a positive inspiratory pressure). The competing efforts result in inefficiency and can cause further respiratory trauma to the already sick animal.

To minimize the invasiveness of the subject/ventilator connection, and reduce the risk of barotrauma, a negative pressure strategy can be employed. Instead of creating positive airway pressure, a negative pressure is generated around the body surface as shown in FIGS. 2A and 2B. FIGS. 2A and 2B respectively show diagrams of methods of ventilation with positive and negative pressure. Such techniques were used on humans in the 1950s and 60's with devices aptly named "iron-lungs." These machines were bulky and inefficient, and therefore quickly outmoded with the advent of positive pressure respirators. However, studies have shown thoracic oscillations to be as effective as tracheal methods in allowing blood gas exchange. An advantage that the negative pressure technique has in newborn mouse ventilation is that the only subject connection is an external cuff around the neck to isolate the body from atmospheric pressure.

Two methods to overcome the problem of ventilator fighting are through patient triggered systems, such as pressure support and negative impedance ventilation, or through high frequency ventilation (HFV).

For human ventilation, patient triggering systems have been developed, where the breathing effort of a patient can be sensed via pressure of flow fluctuations. The effort is then assisted with an inspiratory pressure. Unfortunately, the pressures and flows generated by a newborn mouse are too minute to be sensed reliably. A high threshold would mean a significant time delay in respiratory assistance, while a low threshold would result in excess breathing due to noise.

High frequency ventilation considers an alternate method of breathing by fluctuating respiratory pressures at several times the normal frequency in the range of 10 to 30 Hz. To prevent over-ventilation and hypocapnia, the tidal volume is accordingly reduced by an order of magnitude. This process results in simply oscillating the air within the lungs. Previous studies performed on larger animals have revealed that HFV provides adequate gas exchange in the alveoli, and is therefore an effective method of ventilation.

With these considerations, a miniature HF negative pressure ventilator in accordance with the present invention is presented. However, the small size and fragility of the newborn mice creates a more complex problem. Since minute volumes are generated, the leakage in the system must be minimized in a non-invasive manner. Also, previous systems applied both a positive and negative pressure to the body surface, with a mean pressure equal to atmospheric. These devices used on rats have proven to be an effective means of ventilation. Although such pressure fluctuations are acceptable in small volume generation, if larger volumes are needed, the positive surface pressure could pose a serious threat to the subject by closing the airways.

Since mechanical respiratory attempts have never been made on newborn mice, a large specification range was needed. The ventilator of the present invention is designed to deliver volumes from 0.00 ml to 0.04 ml over a frequency band of 1 Hz (in the normal range) to 100 Hz (higher than the present limits of HFV).

SUMMARY OF THE INVENTION

An object of the present invention is to provide a mechanical respirator for newborn mice or human infants. The necessity for such a device has arisen from, for example, an ongoing project dealing with genetically engineered animals. In the study, the NMDA receptors in the mouse's central nervous system have been knocked out. These receptors are believed to pay a crucial role in the plasticity of the nervous system. Unfortunately, the animals die within the first 10–20 hours after birth, before most major neurological developments have occurred. One documented cause for their death is respiratory failure. Physiological studies have revealed the occurrence of extended periods of apnea, followed by respiratory instability.

With the advent of a mechanical respirator, the lives of these mice may be prolonged, allowing a more thorough study into the roles of NMDA receptors in neuroplasticity and neural development.

In order to successfully ventilate the neonates, it was decided to design a high frequency ventilator due to its proven efficacy. However, it was also important to deliver conventional mechanical ventilation with normal frequency and tidal volume when necessary. These requirements set the criteria for the respirator's operational range:

1. Deliver tidal volumes of 0.00–0.04 ml/breath
2. Frequency range of 1–100 Hz

This was a challenging design problem considering the small body size of the neonatal mice and the minute volume displacement required. Other important concerns are the effects of air leakage in the system, and the need to minimize physical trauma and resultant mortality.

To achieve the design specifications, a negative pressure "iron-lung" strategy was employed due to the small size and the fragility of the neonates. The more widely used intratracheal positive pressure techniques would have been too invasive and traumatic.

A 5–15 ml variable volume chamber is used to modulate the pressure around the mouse's thoracic cavity. This is accomplished by placing a stiff collar around the neck and sealing any small gaps with a non-toxic, non-irritating, adhesive gel. As the mouse is placed into the chamber, body first, the collar creates an air tight seal allowing the possibility for negative external pressures to be applied to the animal's body. A reciprocating piston pump oscillates the pressure within the chamber. By changing the radial displacement of the piston between 0 and 2 cm, the amplitude of the chamber pressure can be varied between 0 and 25 cm $H_2O$) and is detectable by a Motorola MPX 2100 pressure transducer.

A second cam-driven piston acts as a valve, opening the chamber to atmospheric pressure during the positive swing of the pump so as to minimize pressure drift due to valve leakage. This valve normalizes the base pressure despite any systemic leaks (which becomes a concern due to the small volumes being dealt with). The valve piston is held against the cam by a compressive spring.

Both the pump and cam are press fit to a shaft and rotate on two high speed ball bearings. The shaft is connected to a Kollmorgan U9M4 ServoDisc Motor, which can deliver up to 50 ounce–inches of continuous torque over a frequency range of 0–100 Hz. The motor is velocity controlled with a closed-loop tachometer feedback system. The controller signals a 48 V/8 Amp amplifier to drive the motor.

There were several important considerations in the respirator design. First, the required pressure swing was determined from the volume range specification. Using extrapolated data for the chest wall and lung capacitances and resistances to model the respiratory mechanics of the neonatal mouse, the predicted tidal volume could be determined given a sinusoidal pressure wave. Therefore, knowing the desired tidal volume range, the required pressure range was found.

The pump piston and chamber dimensions needed to achieve the pressure range were then determined. A theoretical model of the pump/chamber system was developed using the ideal gas law and fluid flow equations, assuming a sinusoidal piston motion. From the model, the time response of the chamber pressure was solved by using a 3rd order Runge Kutta numerical integration technique. By altering the piston diameter, stroke length, and chamber volume, the pressure swing was fit to the desired values.

A further finding from these simulations was that as the chamber pressure oscillated, the peak pressure (ideally at atmospheric) shifted higher as a result of leakage. A larger pressure swing yielded a larger offset. In order to reduce the leakage, the gap between the piston wall and piston, and the dead length of the piston within the housing was chosen to minimize pousille and couvette flows into the chamber during an oscillation. The other boundary of these dimensions came from practical considerations (i.e. tolerances).

Even with leakage minimized, the one pump system still yielded positive pressures in the mouse chamber. This posed a problem since such a pressure applied to the mouse's body would serve to close its airways, thereby compromising any ventilatory efforts. Therefore, the second cam driven piston was designed to normalize the baseline pressure shift caused by leakage.

A dynamical analysis was performed on the double piston system over the range of operation in order to determine the peak required torque. Then, motors with a rated torque of at least five times the value were considered in order to confidently control the piston velocity. After looking at several possibilities, the Kollmorgan U9M4 servo motor with 48 v/8 Amp amplifier was utilized.

BRIEF DESCRIPTION OF THE DRAWINGS

FIG. 1 shows graphical representations of breathing samples for newborn mice;

FIGS. 2A and 2B respectively show diagrams of methods of ventilation with positive and negative pressure;

FIGS. 9A and 9B respectively show schematic block diagrams of the normalizing valve in closed and open settings;

FIGS. 10A and 10B respectively show cam designs with a 1.3 cm base circle and a 0.8 cm base circle;

FIG. 11 shows a graph of pressure angle profiles for the cam designs of FIGS. 10A and 10B;

DETAILED DESCRIPTION OF THE ILLUSTRATED EMBODIMENTS

Figure 3:
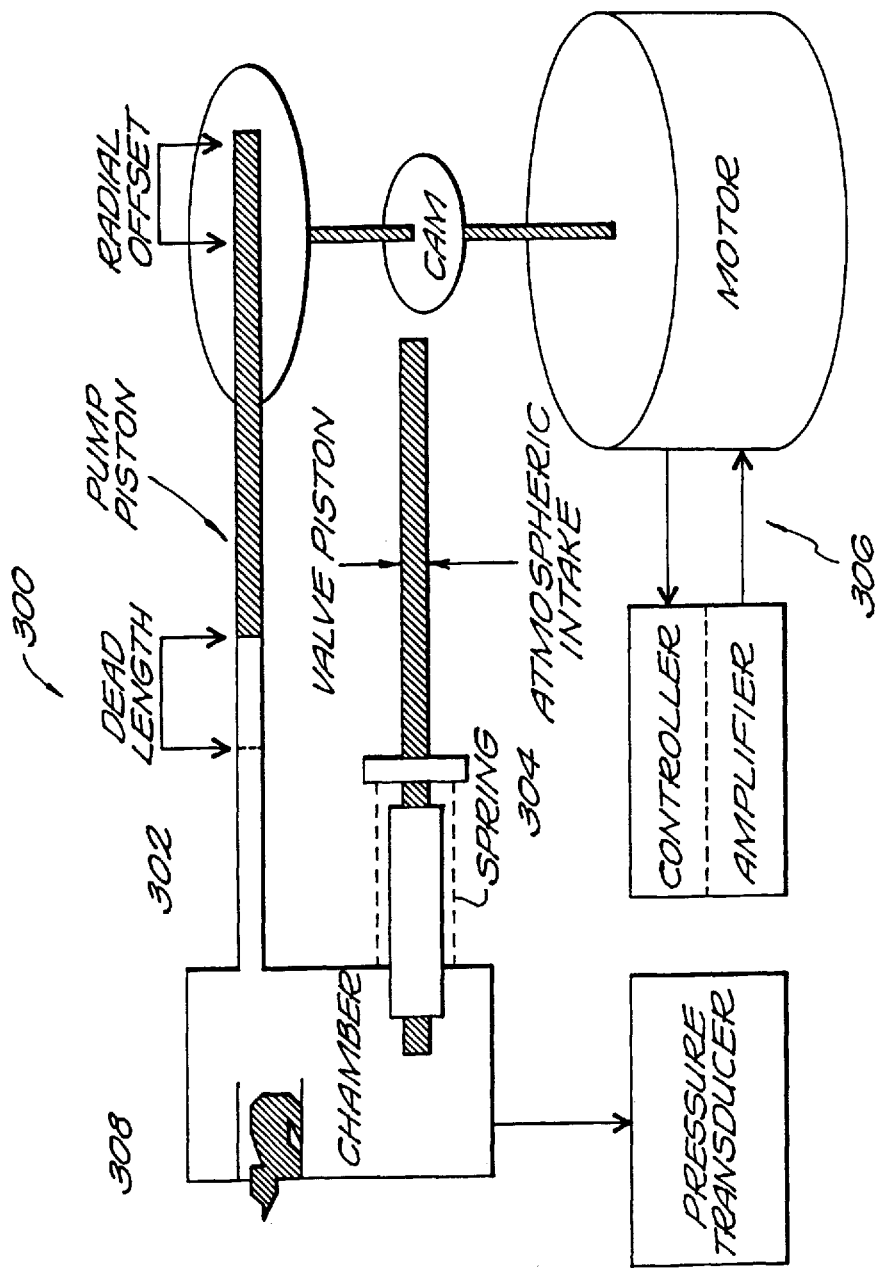
FIG. 3 shows an operational block diagram schematic of the mechanical ventilator in accordance with the present invention.

FIG. 3 shows an operational block diagram schematic of the mechanical ventilator 300 in accordance with the present invention. The device has four major subsections: the pressure generating piston assembly 302, the pressure normalizing valve assembly 304, the motor and controller 306, and the mouse chamber 308. Each assembly is discussed in detail hereinafter.

Figure 4:
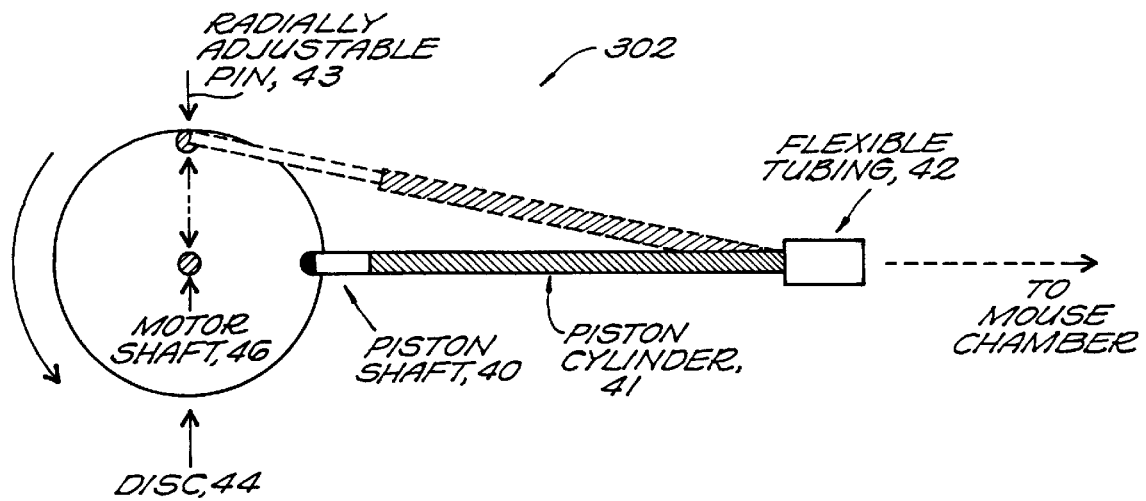
FIG. 4 shows a schematic block diagram of the pressure generating piston assembly of the present invention.

FIG. 4 shows a schematic block diagram of the pressure generating piston assembly 302. The assembly consists of a piston 40 hinged at one end via flexible tubing 42, and to a radially adjustable pin 43 mounted on a 6 cm diameter aluminum disc 44 at the other. The piston comprises an 10 cm long brass shaft with an outer diameter of 0.49 cm sliding in a 9 cm long brass cylinder 41 with an inner diameter of 0.51 cm. The piston head is attached to the adjustable pin which can move radially on a screw track. Since the other end of the piston is fixed translationally by the flexible tubing, the radial adjustment allows the stroke length of the piston to be varied by the simple relation:

$$\text{Stroke} = 2 * \text{Radial location} \tag{1}$$

The aluminum disk is press fit to a 3 mm axle or motor shaft 46. By rotating the disk at a constant velocity, the piston cycles in a sinusoidal motion given by:

$$x = x_o \sin(wt) \tag{2}$$

where x is the piston position, $x_o$ is the radial offset, w is the disk angular frequency, and t is time.

Figure 5:
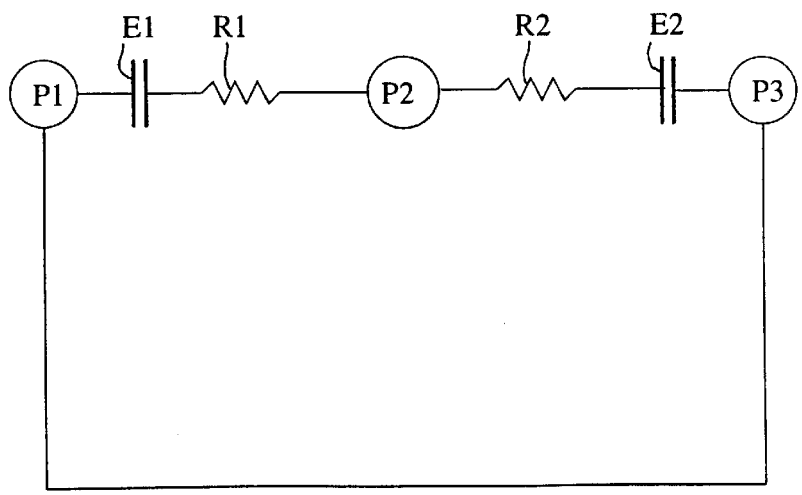
FIG. 5 shows an electrical circuit equivalent of animal respiratory mechanics.

In order to find the dimensions of the piston assembly, the required pressure swing that are needed to be generated in order to create tidal volumes from 0.00 ml to 0.04 ml were found. Obviously, a 0 ml volume translates to a 0 cm $H_2O$ pressure variation. To find the upper pressure limit, the mechanical nature of the newborn mouse respiratory system was considered. The system can be modeled by the electrical circuit shown in FIG. 5.

P1 represents the external pressure and chest wall effort (assumed to be zero if the animal is not breathing), P2 is the pleural pressure, and P3 is the airway pressure. R1 and E1 are the resistive and elastic parameters of the chest wall respectively, and R2 and E2 are the similar parameters for the lung and airways. Since the goal of negative pressure ventilation is to vary P1 in order to generate a volume, P2 is of no consequence. This allows R1 and R2 to be lumped into a total respiratory resistance, Rt, and E1 and E2 into a total elastance, Et.

The governing differential equation for this simplified system is:

$$R_t q + E_t \int_{t1}^{t2} q = P1 + P3 \tag{3}$$

where q is the flow through the system, t1 is the time at the start of inspiration, and t2 is the end inspiratory time. The integrated flow term over an inspiratory cycle represents the tidal volume. For negative pressure ventilation, P3 remains constant at atmospheric pressure.

The parameters Rt and Et were estimated using general scalable equations for mammals:

$$R_t = 24.4 m^{-.70} \tag{4}$$

$$E_t = \frac{1}{1.56 m^{1.04}} \tag{5}$$

where m is the mass of the mammal in kg. Using an average newborn mass of 0.0015 kg from previous studies, Rt and Et were determined to be 2.31 cm $H_2O$/(l/sec) and 554 ml/cm $H_2O$ respectively.

The desired tidal volume is given to be 0.04 ml in equation 3. Therefore, assuming P1 to be a sinusoidal negative gauge pressure (as would be generated by a piston motion described in equation 2), a simple program was written to numerically solve equation 3 using Euler's method (see Appendix A). By giving the amplitude of the pressure swing, the flow and tidal volume were found for a single inspiratory cycle. The process was iterated using different pressure amplitudes until the desired tidal volume was attained. The pressure range for the pressure generating piston was determined to be from 0 to 25 cm H20 (though a pressure of 22.8 cm H20 was sufficient to generate to 0.04 ml tidal volume).

The assembly dimensions were found by constructing a mathematical model of the piston system. The model assumed that the air behaved as an isothermal ideal gas governed by the ideal gas law:

$$PV = mRT \tag{6}$$

where V is the volume of the body cavity isolation chamber, P is the absolute pressure in the chamber, R is the gas constant (287 J/kgK for air), m is the mass of air in the chamber, and T is the air temperature. As the piston oscillates, the pressure, volume and mass can vary, though the temperature is constant, due to the isothermal assumption. Therefore, equation 6 can be expressed in a more useful differential form:

$$dP = \frac{dmRT - PdV}{V} \tag{7}$$

The volume change, dV, is described by the equation:

$$dV = \dot{x}\pi r^2 \tag{8}$$

where x is the time derivative of the piston position, x, or velocity, and r is the radius of the piston. As seen in equation 2, the general piston motion is sinusoidal. However, to describe the actual motion, the phase and equilibrium position must be determined from the initial conditions. The piston starts in a compressed state, and rotates, generating a negative pressure until fully extended (the stroke length). Considering these conditions, the piston motion is:

$$x = x_o - x_o \cos(wt) \tag{9}$$

$$\dot{x} = dx \tag{10}$$

$$= wx_o \sin(wt) \tag{11}$$

The change in mass, dm, in equation 7, can be determined from fluid flow considerations. Combining the Cuvette and Pousille flow equations, the relation:

$$dm = 2p\pi r \left[ \frac{dxh}{2} - \frac{h^3(P_{gauge})}{12\mu a} \right] \tag{12}$$

is found, where p is the density of air (1.204 kg/m^3), $\mu$ is the viscosity of air (1.82e-5 Pas), Pgauge is the gauge chamber pressure, r is the average piston radius (shaft and cylinder), h is the gap size between the piston shaft and cylinder, and 1 is the length of the gap, geometrically related to the piston motion by:

$$a = 2x_o + a_o - x \tag{13}$$

where $a_o$ is the nominal length of the piston shaft in the cylinder at all times during maximal stroke. The first bracketed term in equation 12 is a result of mass transfer due to the generated pressure gradient across the gap while the second term is the leakage caused by the relative motion between the piston shaft and cylinder wall. The first term dominates equation 12 due to air's low viscosity.

The theoretical model described by equations 7, 8, 10, and 12 was then numerically solved using a pre-defined 3rd order Runga Kutta function (ODE23) available in MATLAB (the program listing is given in Appendix B). The variables that could be adjusted were the stroke length, the shaft radius and length, the cylinder radius and length, and the volume of the mouse chamber. Each parameter needed to be considered in order to determine suitable dimensions.

The shaft/cylinder gap size (ideally 0 for no leakage), was limited by achievable tolerances and cost considerations. Another concern was that the stroke length needed to be small (due to size concerns and jamming problems dependent on the piston length), yet large enough for discernible radial piston positions to allow the pressure to be varied accurately between the 0 to 25 cm H20 range. Finally, by making the shaft and cylinder longer than the stroke length (thereby lengthening the gap), the leakage could be reduced by increasing resistance to Pousille flow. Again, the lengths could not be too long, for practical considerations.

Figure 7:
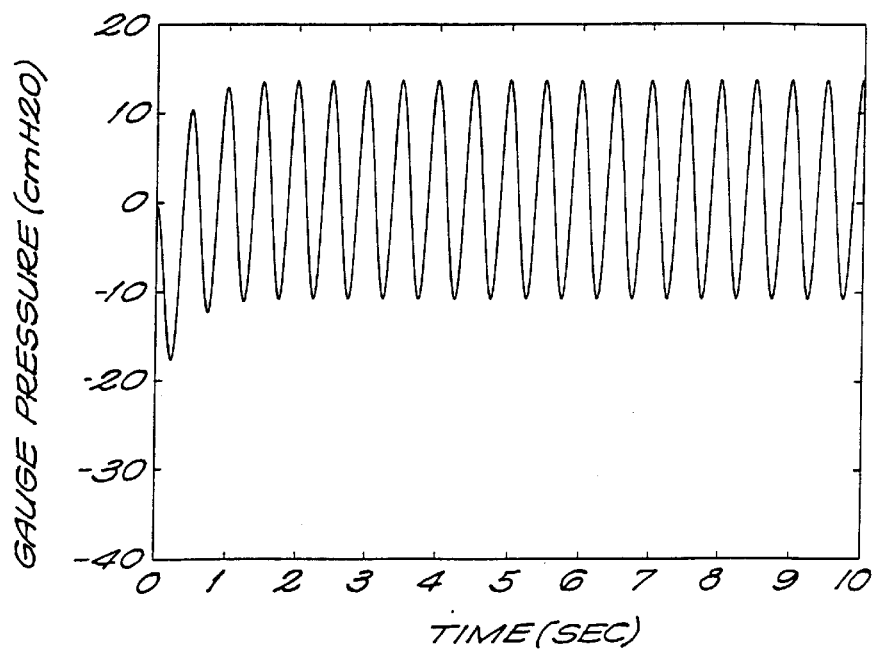
FIG. 7 shows a graph of theoretical pressure profile for 0.08 cm gap (high leakage)
Figure 8:
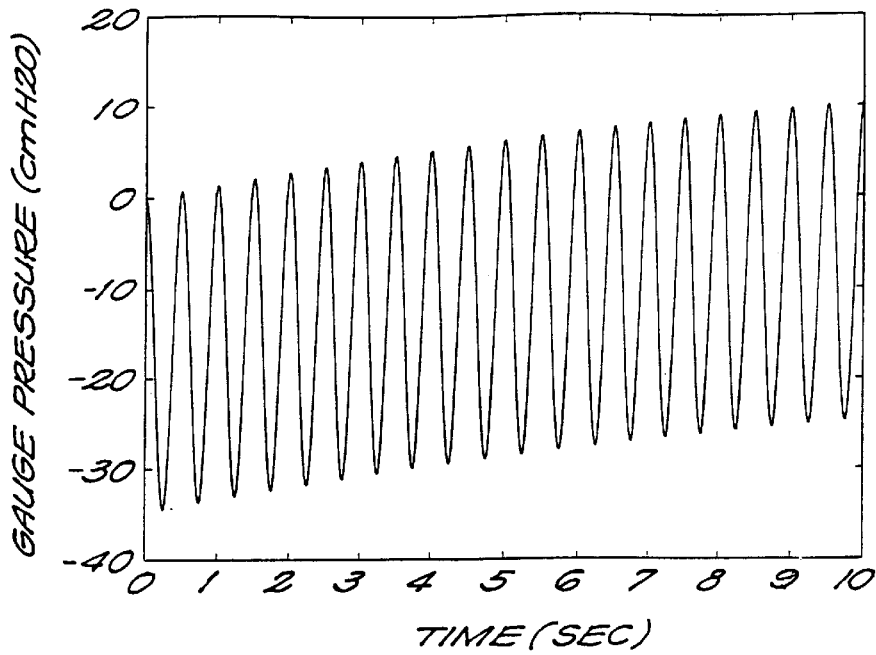
FIG. 8 shows a graph of theoretical pressure profile for 0.03 cm gap (low leakage)

With these limitations, the piston radius and chamber volume were adjusted to ensure the maximum pressure of 25 cm H20 could be achieved. After several runs, suitable parameters were obtained (piston shaft radius=0.00245 m/piston cylinder radius=0.00255 m/ stroke length=3 cm/ nominal gap length=5 cm/ chamber volume=15 ml). Exemplary test results are shown in the graphs of FIGS. 6–8.

Figure 6:
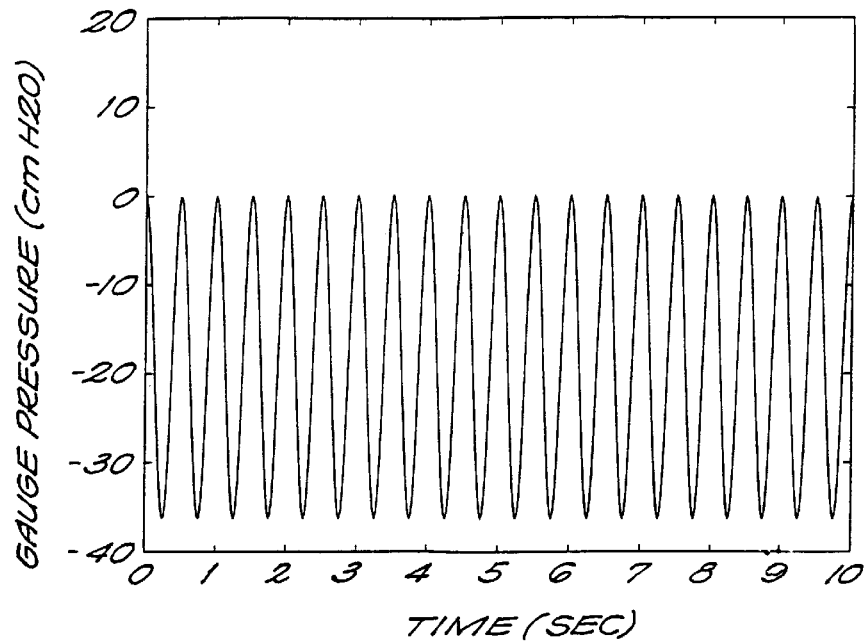
FIG. 6 shows a graph of theoretical pressure profile for 0.00 cm gap (no leakage)

FIG. 6 depicts an unrealistic simulation with no gap, and therefore, no leakage. The pressure starts at 0 cm $H_2O$ gauge pressure (one atmosphere) and drops to 37 cm H20, before rebounding back to the base-line. FIG. 7, on the other hand, has a large gap, of 0.08 cm. As the negative pressure is generated, leakage causes mass to be transferred into the chamber. Therefore, when the piston rebounds, a positive pressure is generated, causing the subsequent swing to start from an elevated level. With a large gap, this base-line shift settles quickly as the gauge pressure oscillates about 0 cm H20. The maximum pressure swing achieved is 18 cm $H_2O$, over half that of the no gap case. Since all systemic leakage was not modeled, it is clear that the piston must be overdesigned to ensure the full 25 cm $H_2O$ specification can be met. Finally, FIG. 8 shows a realistic simulation, with a 0.02 cm gap. The pressure in the first few oscillations closely resembles the no gap case. Unavoidable, there is still a pressure drift, though it has a much longer time constant than the large gap scenario. The base-line shift lead to the development of a pressure normalizing valve, as described in the following section.

Figure 9A:
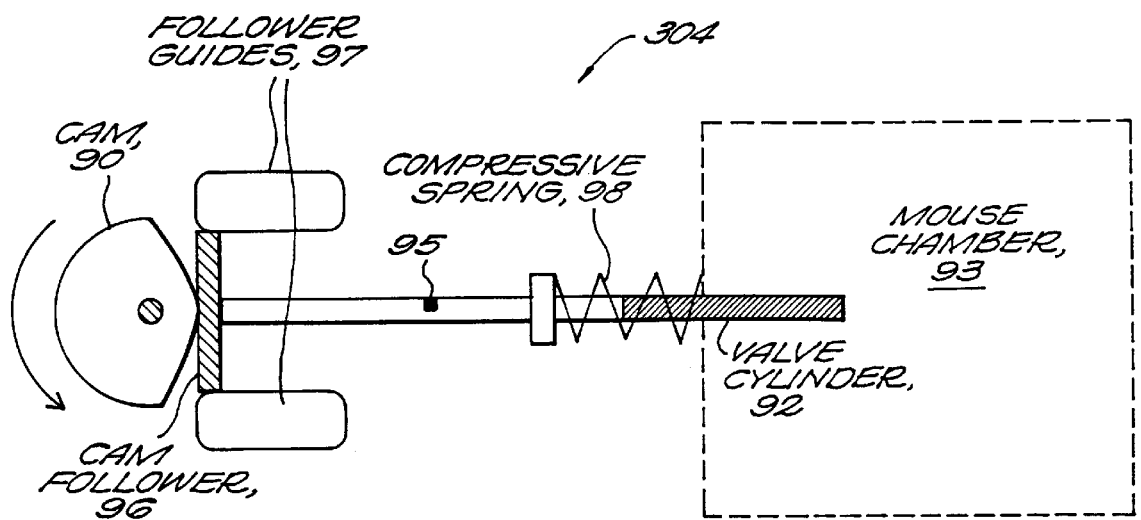

FIGS. 9A and 9B respectively show schematic block diagrams of the normalizing valve in closed and open settings. The components include a cam 90 and a 0.49 cm outer diameter hollow shaft 91 closed at both ends. The shaft is concentric with a 0.51 cm cylindrical port extending 0.7 cm into the mouse chamber. The camshaft has an inlet 94 slit 0.7 cm from the end proximal to the mouse chamber and another outlet 95 on the length of shaft outside the chamber. The cam, which is coaxial to the pressure generating piston disk, drives the shaft providing a 0.7 cm stroke. The cam has been designed to provide the maximal stroke through out the entire positive pressure phase of the pressure generating piston, while retracting during the negative phase. This action allows the mouse pressure to equilibrate with atmospheric pressure throughout the positive phase.

A cam follower 96 (essentially a flat surface perpendicular to the shaft) provides the contact surface between the shaft and cam. The follower is guided by tracks 97 to keep undesirable force components from bending the shaft. A 986 N/m spring 98 holds the cam follower in contact with the cam perimeter.

The need for the valve normalizing piston is evident in FIG. 6–8. As FIG. 8 indicates, even with low leakage, there is an unavoidable pressure drift caused by leakage in the system. Additionally, the simulations deal with leakage through the piston gap, though there are undoubtedly other problematic areas, such as the ventilator/mouse connection The pressure drift is detrimental in two ways. Firstly, the upward shift means the desired negative pressure cannot be reached without changing the piston parameters (seen in FIG. 7). More importantly, the positive pressure generated, which upon equilibration is equal in magnitude to the negative pressure, serves to compress the body cavity, thereby closing the subject's airways. Such an effect is detrimental to any ventilatory efforts.

In larger ventilators, the leakage is not a major concern since the volumes dealt with are much larger than the mass transfer due to leakage. However, the small volume needed for neonatal mouse respiration necessitates that the leakage problem be considered.

In order to eliminate the effects of mass transfer, the chamber pressure must be normalized with each cycle. Two methods considered were the cam valve design and a solenoid valve mechanism. The solenoid was rejected since it would require the use of additional actuators, increasing the system complexity. Also, such a mechanism would need a triggering cam similar to the present design. Therefore, to minimize complexity and redundancy, the cam valve method was chosen.

The cam was designed to have a maximum outer radius of 2 cm, equal to the maximum radial offset of the pressure piston (a 4 cm stroke was allowed for the prototype design). This guaranteed size consistency regardless of later design changes. Another requirement was the cam stroke needed to be as large as possible in order to minimize leakage through the normalizing valve slit during the negative pressure swing (the larger the stroke, the further the slit could be placed from the chamber end, thereby increasing resistance to mass transfer). The limiting factor on the stroke length, other than the over all size limit of 2 cm on the cam radius, was the pressure angle. The pressure angle is defined as the angle between a line normal to the cam follower trace (essentially the cam surface) and the line drawn from the cam's center to the cam/follower contact point. A large pressure angle creates significant torque on the camshaft, resulting in inefficiency, and therefore is generally limited to under 30°.

Two possible cam designs, one with a base circle of 1.3 cm (stroke of 0.7 cm) and one with a circle of 0.8 cm (stroke 1.2 cm) are shown in FIGS. 10A and 10B. The pressure angle profiles for the cams were determined geometrically and are presented in FIG. 11. The first cam, represented by the solid line, has a maximum pressure angle of just under the 30° limit (28.5°). The second cam (dashed line) has a pressure angle exceeding the given limit (45°). After such considerations, the first design was selected. A displacement profile of the chosen cam is given in FIG. 12.

Another design consideration in the pressure normalizing valve assembly was the spring. A spring with a sufficiently large spring constant was required to ensure the cam follower would remain in contact with the cam surface. Such selection would reduce the chattering and wear of the cam assembly, and more over, keep the valve timing in synchronization with the pressure generating piston.

To find the proper spring, the natural frequency of the valve assembly was found by the relation:

$$w_n = \sqrt{\frac{k}{m}} \quad (14)$$

where k is the spring constant and m is the mass of the moving shaft and cam follower. The maximum frequency was known to be 628 rad/sec (100 Hz) and the mass was 0.01 kg, Therefore, k was 3950 N/m. Since the 100 Hz was an extreme limit, it was decided to tailor the spring for 50 Hz speed resulting in a 986 N/m spring constant. This would enable higher speeds to be achieved, though chattering would occur. However, it would also decrease the energy needed to drive the system considerably.

Figure 13:
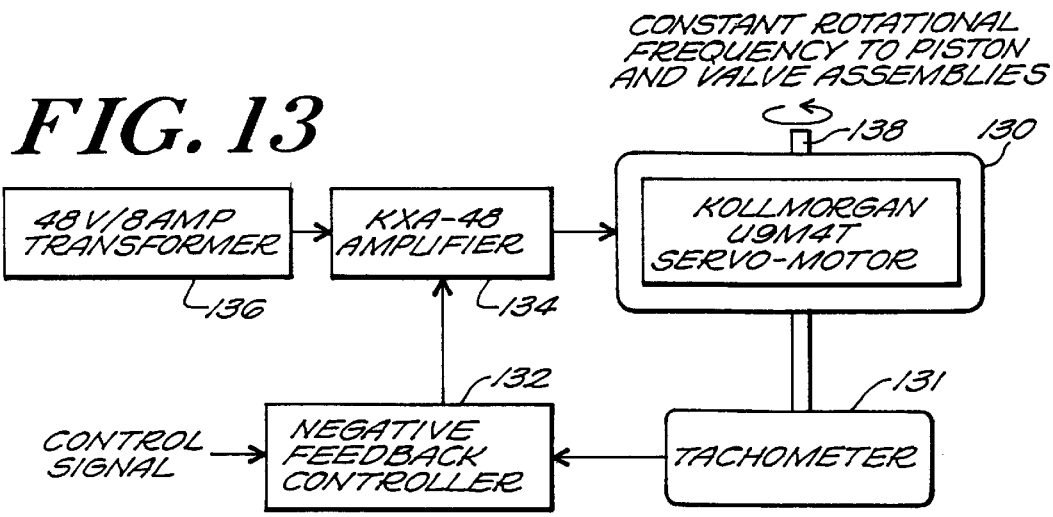
FIG. 13 shows a schematic block diagram of the motor/controller system.

A schematic of the actuator system 306 is shown in FIG. 13. The actuator used to drive the ventilator is a KOLLMORGAN U9M4T servobrush motor 130. It is velocity controlled with tachometer 131, 132 feedback by a KXA-48 amplifier 134. The system is powered by a 48 v/8 amp power transformer 136. The motor shaft 138 is connected to a 3 mm steel shaft which drives the cam and pressure piston assemblies via an aluminum joiner. Both shafts are press fit in the joiner and held snugly with screws. The 3 mm shaft rotates in two greased ball bearings that are separated by 2 cm.

Motor selection depended on the ability to provide adequate torque over the 0–100 Hz operating range. In order to determine the torques, both the pressure generating piston and the normalizing valve were considered.

Figure 14:
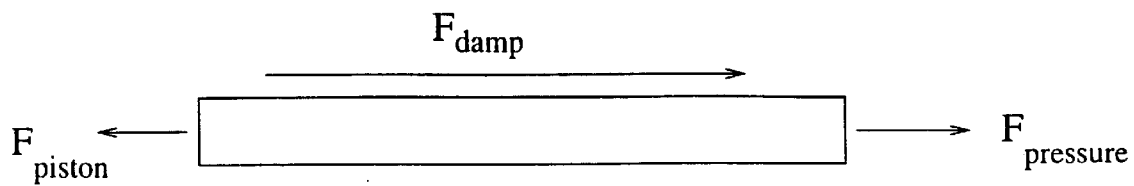
FIG. 14 shows a piston free body diagram.

The forces required by the pressure piston can be found by a free body diagram, as seen in FIG. 14: In FIG. 14 $F_{piston}$ is the force generated by the motor to drive the piston, $F_{damp}$ is viscous damping resulting from piston motion, and $F_{pressure}$ is the force created by the chamber pressure acting on the piston face. $F_{damp}$ and $F_{pressure}$ are defined as:

$$F_{damp} = \dot{x} \quad (15)$$

$$F_{pressure} = P\pi r^2 \quad (16)$$

where c is the damping constant (assumed to 0.1 Ns/m), x is the velocity of the piston given by equation 11, P is the time variant chamber pressure, approximated by a cosine wave of stroke dependent amplitude, and r is the piston radius.

From Newton's Second Law, the sum of these forces yields the acceleration of the piston shaft:

$$m_1 \ddot{x} = F_{piston} - F_{damp} - F_{pressure} \quad (17)$$

$m_1$ is the mass of the piston, and x is its acceleration, found by time derivative of equation 11. Therefore, the required motor force needed to drive the piston assembly can be found.

Figure 15:
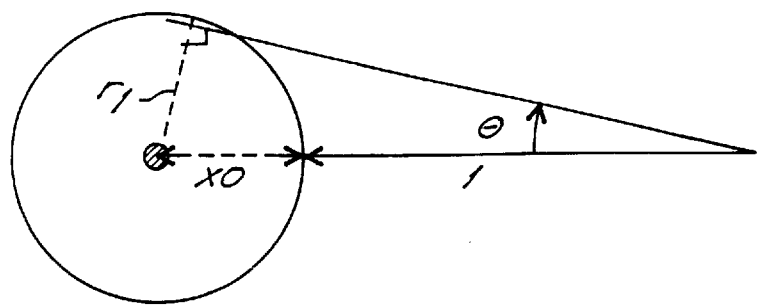
FIG. 15 shows a schematic block diagram of a fulcrum.

To translate this force into the torque on the motor shaft, the fulcrum must be found through geometric considerations, as revealed in FIG. 15. The fulcrum, r1, is given by:

$$r_1 = (x_o + l)\sin\Theta \quad (18)$$

where $x_o$ is the radial offset, l is the initial length of the piston from the flexible hinge to the aluminum disc, and Θ is the time variant angle between the nominal piston position and that at any given time. Since the piston cycles at a constant frequency, Θ is given by:

$$\Theta = \tan^{-1}\left(\frac{x_o}{x_o + l}\right)\sin(2wt) \quad (19)$$

Finally, the piston torque, $T_{piston}$ is determined by:

$$T_{piston} = F_{piston} r_1 \quad (20)$$

With this, the valve torque must be considered.

Figure 12:
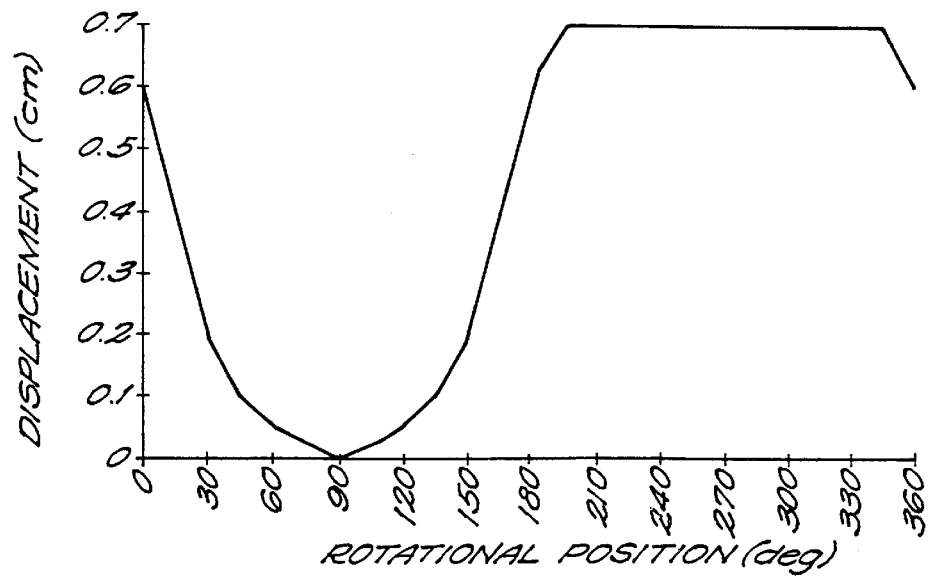
FIG. 12 shows a graph of the displacement profile of selected 0.7 cm stroke cam.

The forces needed to actuate the valve arise from spring, inertial, and dissipative forces. The spring force generated by the 986 Nm compressive spring is simply:

$$F_{spring} = ky \quad (21)$$

in accordance with Hooke's Law, where y is the compression of the spring, described by the displacement function given in FIG. 12. The displacement function can be approximated by the equations:

$$0 \leq w < \pi :: y = 0.0035 \cos 2wt + 0.0035 \quad \pi \leq w < 2\pi :: = 0.007 \quad (22)$$

$F_{spring}$ holds the cam and cam follower in contact, resulting in the principle dissipative force, $F_{friction}$. This columbic friction is proportional to the contact force ($F_{spring}$), and is therefore:

$$F_{friction} = \mu F_{spring} \quad (23)$$

In the equation, u is the frictional coefficient between the aluminum cam and plexiglass cam follower (determined experimentally to be 0.15).

Finally, the inertial term of the valve shaft must be considered. As seen in the piston derivations, the inertial force is $$F_{inertia} = m_2 \ddot{y} \quad (24)$$

where $m_2$ is the mass of the valve shaft and cam follower, and $\ddot{y}$ is the acceleration found by the second time derivative of equation 22. However, since there is no definitive connection between the cam and the follower, the motor can only provide positive accelerations (extending the valve), while the retractive accelerations are provided by the compressive spring. Therefore, only the period $\pi/4 \leq \cdot 3\pi/4$ need be considered in the inertial force calculations.

Figure 16:
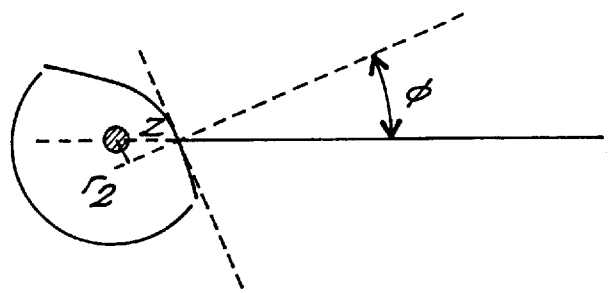
FIG. 16 shows a schematic block diagram of a valve fulcrum arm.

As in the piston derivations, the fulcrum arm upon which these forces act must be determined in order to find the required motor torque. Both $F_{inertia}$ and $F_{spring}$ act on the arm, r2, indicated in FIG. 16. r2 is derivable by:

$$r_2 = z \sin \phi \quad (25)$$

where $\phi$ is the position variant pressure angle seen in FIG. 11A, and z is the distance from the cam center to the contact point. z is related to the displacement, y, through addition of the base circle (1.3 cm).

The arm which the frictional force acts on can be approximated by z since the cam surface curvature is slight.

Therefore, the torque required to operate the valve system, $T_{valve}$ is given by $$T_{valve} = (F_{sping} + F_{valve})r_2 + F_{friction}^z \quad (26)$$

and the total torque needed to drive the ventilator is $$T_{total} = T_{piston} + T_{valve} \quad (27)$$

In these derivations, the bearing and motor damping are assumed to be negligible in relation to the other components. Also, since the ventilator operates at a constant velocity, the transient factors (such as the motor inertia) were not considered.

Figure 17A:
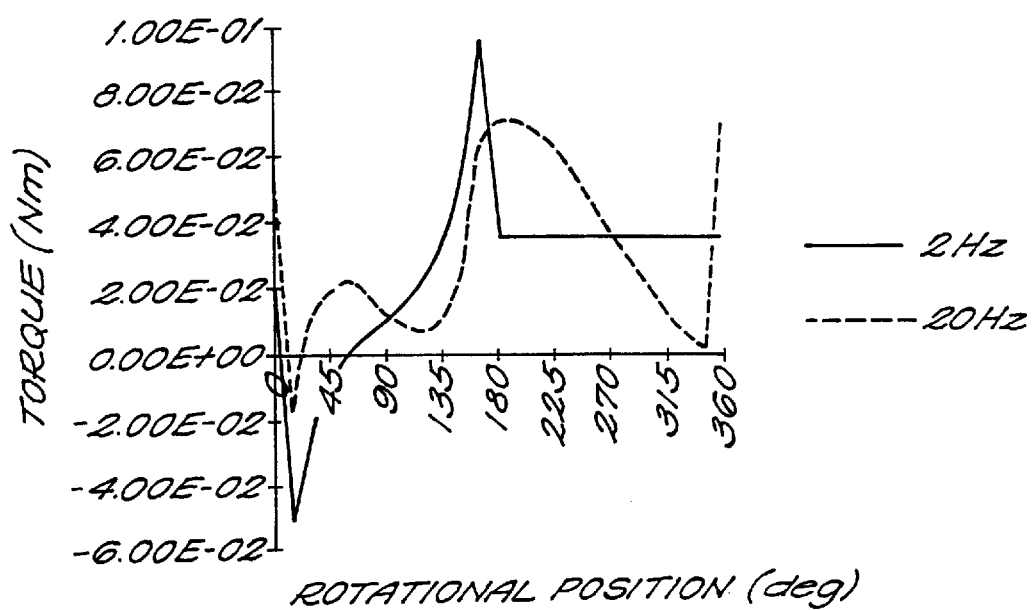
FIGS. 17A and 17B respectively show graphs of torque variance for 25 cm and 5 cm $H_2O$ pressure generation at various frequencies.
Figure 17B:
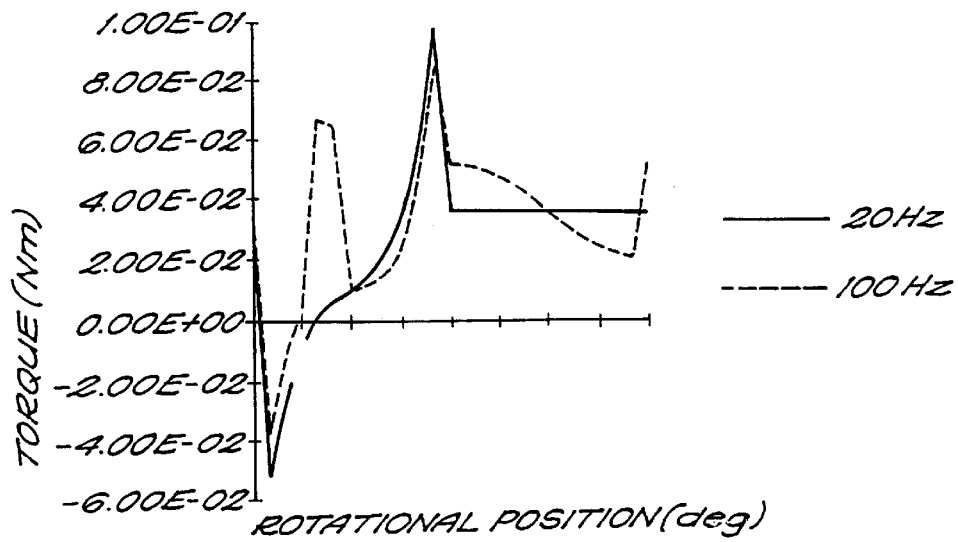
Figure 18:
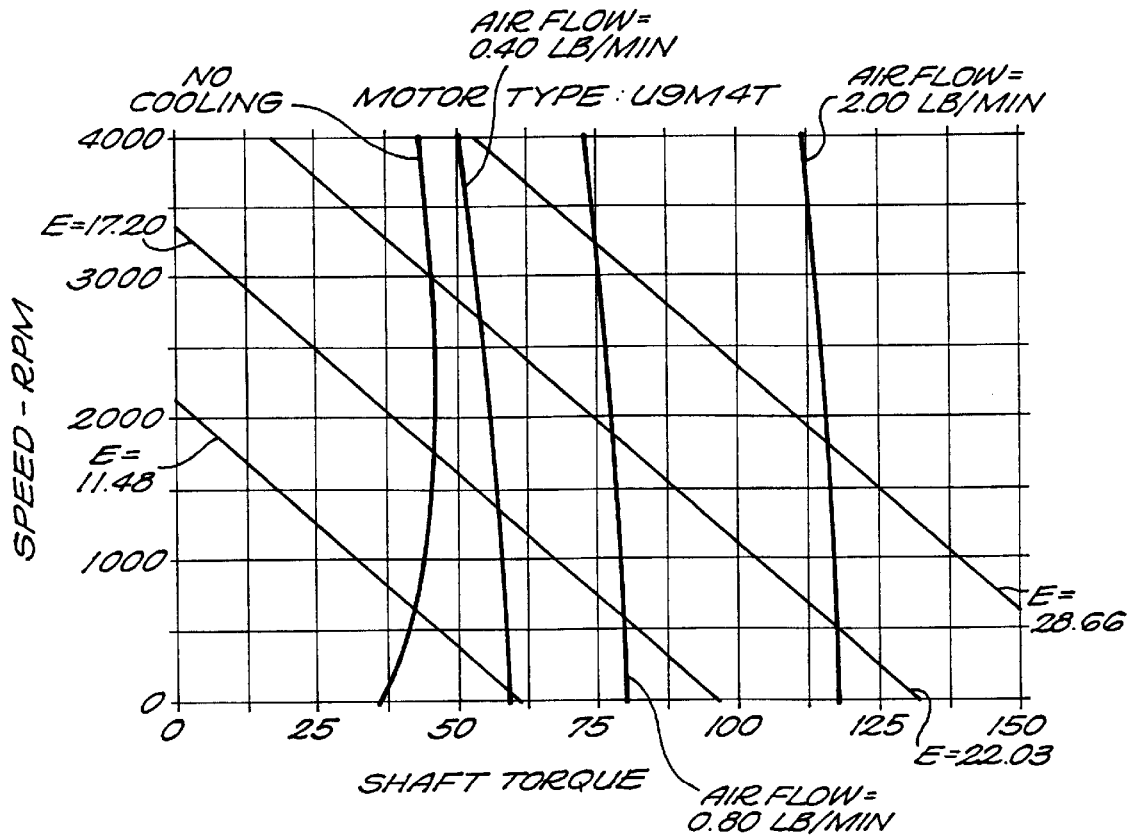
FIG. 18 shows a graph of torque vs. frequency for the motor.

The theoretical torques required over a given cycle are plotted in FIGS. 17A and 17B for various ventilator operation setups. The solid line in FIG. 17A indicates normal ventilation at a frequency of 2 Hz and a pressure swing of 25 cm H20. The torque profile is dominated by spring force considerations, as is witnessed by the torque flips when the spring goes from a compressive to an extensive state. This spring dominance at low frequencies was the reason the valve was designed to run smoothly at about 50 Hz instead of 100 Hz. Doubling the frequency would quadruple the spring force. Therefore, there would be excessive power loss even though the ventilator would rarely be run at such high frequencies.

As the frequency is increased, the inertial elements become more relevant. The dashed line in FIG. 17A reveals a sample at 20 Hz with 25 cm $H_2O$ pressure generation. The distinctive peaks are smoothed by the accelerations and decelerations of the shafts. Such operation (high frequency, high pressure) would severely over-ventilate the neonatal mice. Therefore, the solid line in FIG. 17B, shows a more realistic 20 Hz trial with a 5 cm $H_2O$ pressure variation. Again, since this is accomplished by reducing the stroke length, the accelerations of the piston are not as great and the inertial term is minimized, yielding a plot similar to the normal ventilation trial in FIG. 17A. Finally, the dashed line in FIG. 17B shows an example at the maximal frequency of 100 Hz, where again, the inertial terms can be seen. In each figure, there is a constant offset from 0 Nm (witnessed at positions $>\pi$), which is a result of the friction between the cam and cam follower.

By finding the peak and minimum torques, the limiting bounds were determined to be between 0.1 Nm to −0.06 Nm. Since there is a considerable amount of variation in the torque, either a high inertia system with nominal feedback or a high torque motor with good feedback can be used to provide a constant rotational velocity. The inertia method, acting as a torque buffer, would be efficient and operate well at high frequencies. However, such a system would only work at low frequencies if an extremely high rotational inertia was used, and therefore is impractical. The high torque motor with feedback and a small mechanical time constant is more suitable to this application considering the wide frequency range. In order to ensure the motor's capability to drive the ventilator smoothly, a maximum continuous torque of at least three times the torque variance was used in motor selection.

In order to provide this torque, several types of motors were considered: DC brush, DC brushless, and AC inductance motors. The AC induction and DC brushless had the advantage of wear resistance. Since neither had brushes, their operation time was limited by bearing life. However, the AC induction motor is much more difficult to control than with simple tachometer feedback. Similarly, the DC brushless motor is much more complex to control, and therefore considerably more expensive than a brush motor with similar torque and frequency characteristics.

Since it is possible to replace worn brushes, the life span was less of an issue than price and complexity. After looking at several possibilities, the KOLLMORGAN U9M4T DC servobrush motor was selected (estimated to have a brush life of over year under continuous operation under maximal stress). The motor can operate continuously over a range from 0 to 4000 rpm (67 Hz), providing a torque of around 40 oz in (0.28 Nm) with no ventilation. If cooling or non-continuous operation is an option, the torque can be increased by quite a margin. Additionally, since the 4000 rpm is achievable at under 30 V, and the KXA-48 is a 48 volt amplifier, speeds of 100 Hz can be easily reached, though there is a slight drop in torque.

To control the motor, an integrated tachometer with an output voltage of 2.25 V/KRPM is used. This tachometer provides a feedback signal to the KXA-48 amplifier, set in a velocity control mode (as opposed to torque control), which in turn drives the motor. The amplifier switching frequency is 40 kHz, well beyond the need for this application. The motor has a mechanical time constant of 20.5 msec. Though this yields a lower than desired frequency of around 50 Hz (ideally, it would be 4 times the desired controllable frequency if simple feedback is used), the required 100 Hz can be achieved via the KXA phase adjust control strategy.

Figure 19:
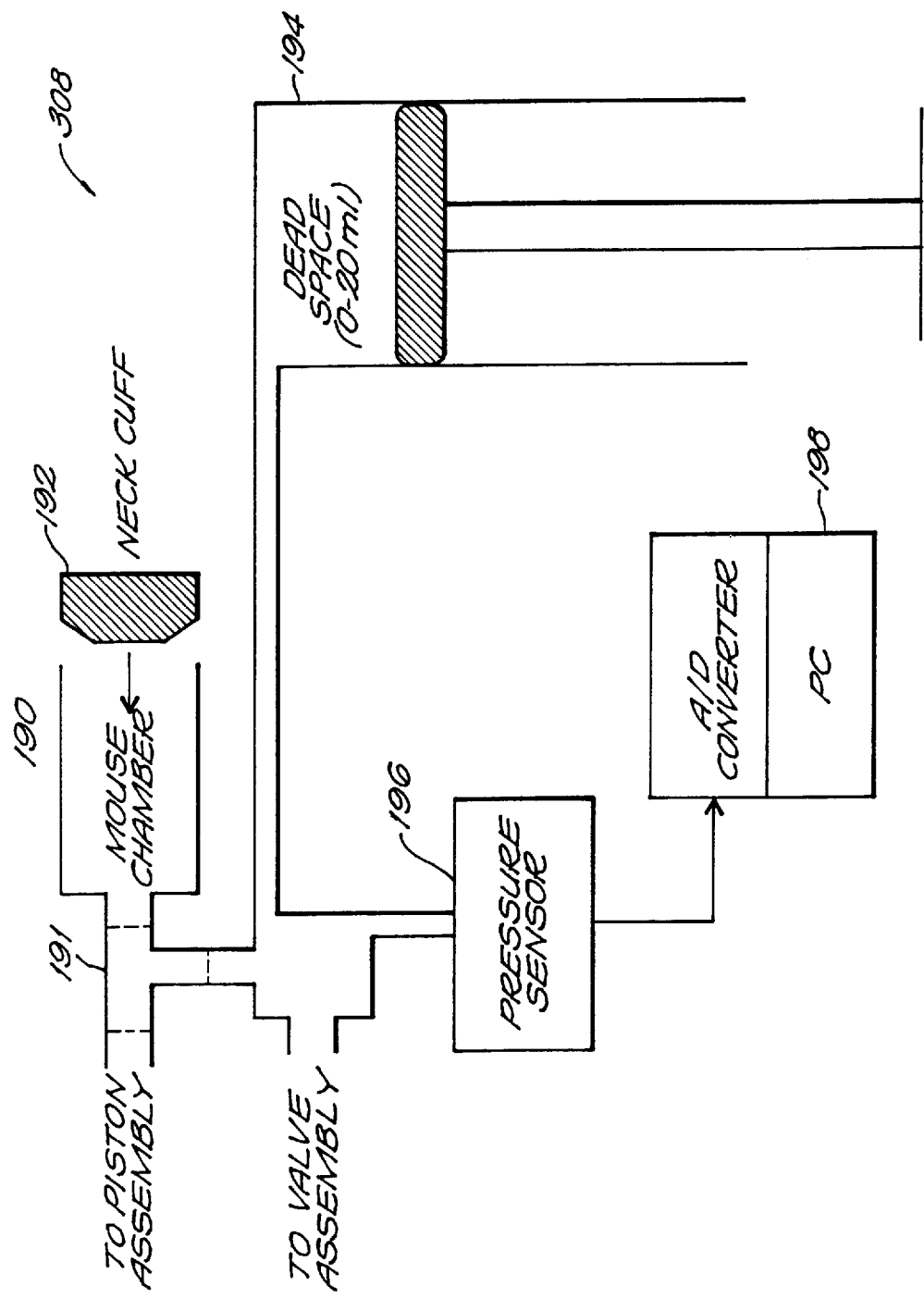
FIG. 19 shows a schematic block diagram of the mouse chamber.

A schematic block diagram of the mouse chamber 308 can be seen in FIG. 19. The mouse chamber is made of two compartments. The first is a 3 ml plastic cylinder 190 which is detachable from the apparatus. It is connected via a three way valve 191 to the pressure generating piston assembly. The unconnected end allows a neonatal mouse to be positioned inside the cylinder. To stop leakage, a rubber cuff 192 is first placed around the newborn's neck, and then sealed with a dental adhesive. Then, the mouse's body is placed within the chamber, with the rubber fitting snugly in place.

A second compartment 194 is connected to the third stem of the three way valve, and houses the chamber end of the normalizing valve. This compartment has an adjustable volume of 20 ml which acts as a dead space. By varying the volume, the mouse chamber pressure can be varied while the ventilator is in operation, though to achieve the large pressure variations, the stroke length must be adjusted.

A silicon sensor 196 (Motorola MPX 2100) is connected to the chamber and allows for a real time pressure signal to be monitored either on an oscilloscope or computer 198.

The required size of the mouse chamber was determined in conjunction with the pressure generating piston design. The design required a chamber volume of 15 ml, considering the parameters chosen (piston dimensions and stroke length). The actual chamber is adjustable from approximately 5 ml (3 ml mouse chamber plus 2 ml connection tubes) to 25 ml. This wide range was selected since the theoretical model assumes that leakage occurs only through the piston gap. In reality, other sources (such as the neck cuff) may be present. Therefore, a variable volume allows for pressure calibration. Additionally, the adjustable volume allows for the ventilator pressures to be varied while in operation, since stroke length adjustment requires the motor to be stopped. Finally, the large dead space, as determined empirically, successfully negates the pressure fluctuations created by the valve operation.

Figure 20:
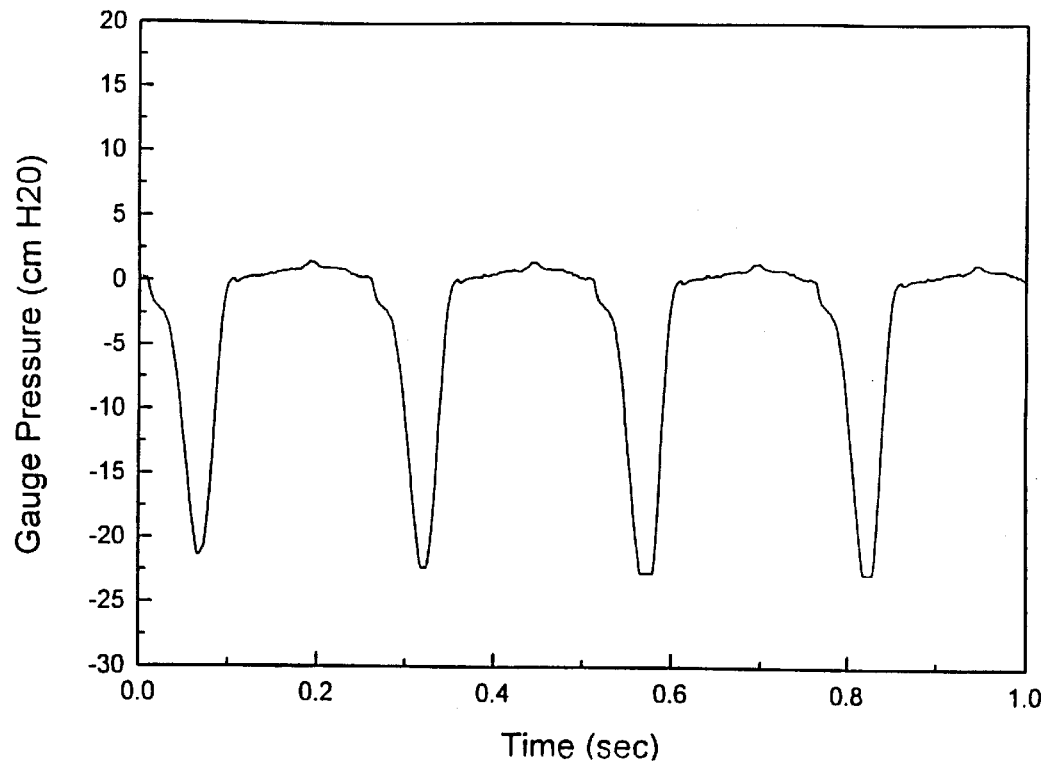
FIG. 20 shows a graph of a pressure profile for low frequency, high pressure operation (4 Hz/22.5 CM $H_2O$)
Figure 21:
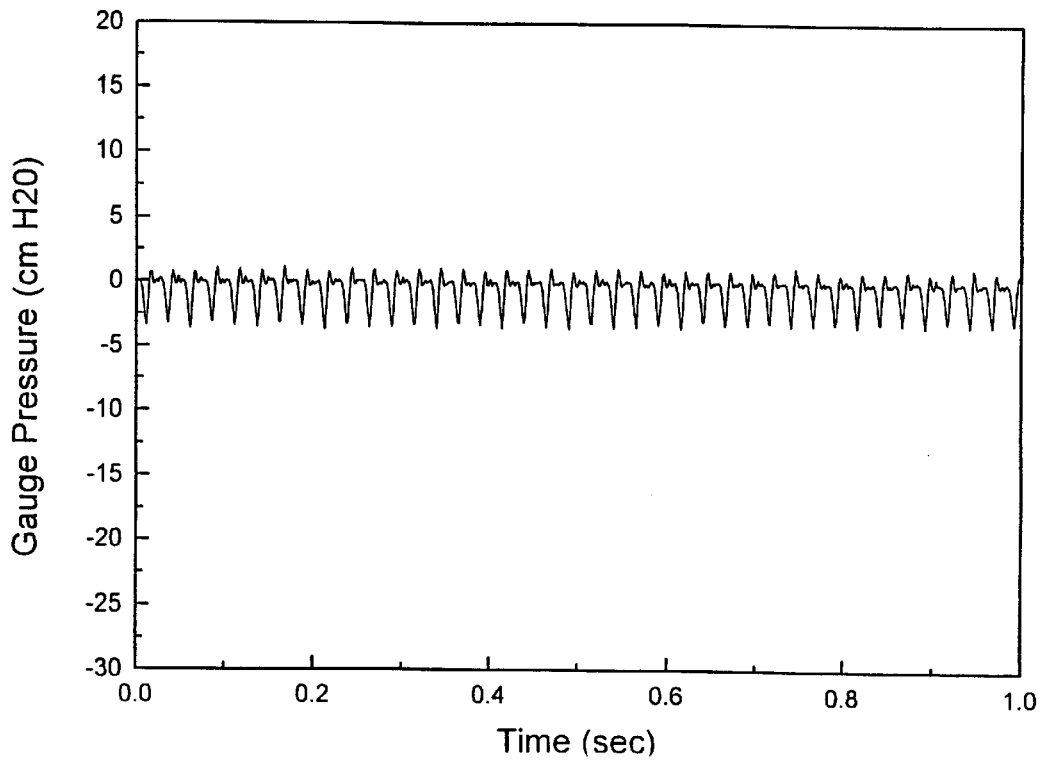
FIG. 21 shows a graph of a pressure profile for high frequency, low pressure operation (40 Hz/3.5 cm $H_2O$)

The ventilator is designed to deliver pressures from 0 to 25 cm $H_2O$ over a frequency range of 1 to 100 Hz. This range was tested by sealing the mouse chamber orifice with a stopper and collecting pressure profile samples with CODAS, a data acquisition program, and a PC. FIG. 20 shows low frequency ventilator operation at a 4 Hz frequency, and a pressure of 22.5 cm H20. The normalizing valve function can be seen by the flat regions in the pressure profile, when a positive pressure would otherwise be generated. FIG. 21 shows the pressure wave form at a frequency of 40 Hz, and a pressure swing of 3.5 cm $H_2O$, qualifying as very high frequency ventilation. Again, the normalizing valve effectively keeps the baseline pressure from drifting, though the line is noisy due in part to systemic vibrations.

Figure 22:
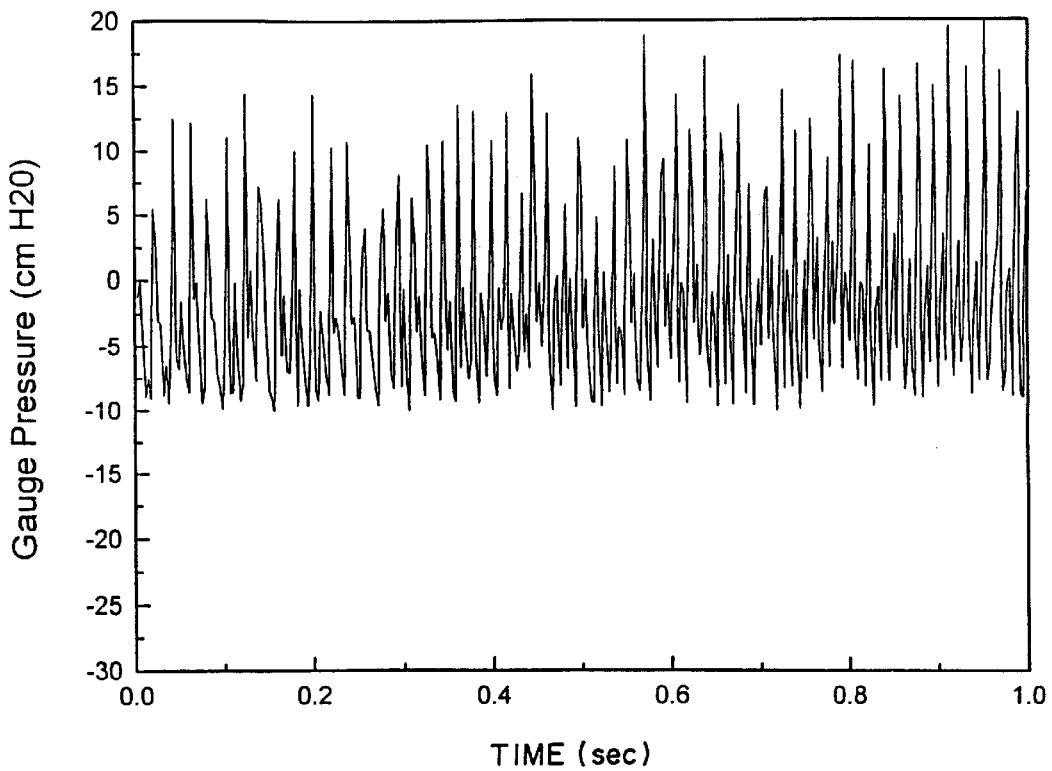
FIG. 22 shows a graph of a pressure profile for 100 Hz operation revealing valve malfunction.

As mentioned in the valve design section, the 986 N/m spring is capable of handling frequencies up to about 50 Hz (some considerations must be made for the damped natural frequency). As the system is pushed past this point, the cam and valve become unsynchronized. The effect of this error can be witnessed through the positive pressures generated in FIG. 22, which shows a trial at 100 Hz. Though this is an undesirable occurrence, it is acceptable so long as volume generation is minimal as discussed in the introduction.

Figure 23:
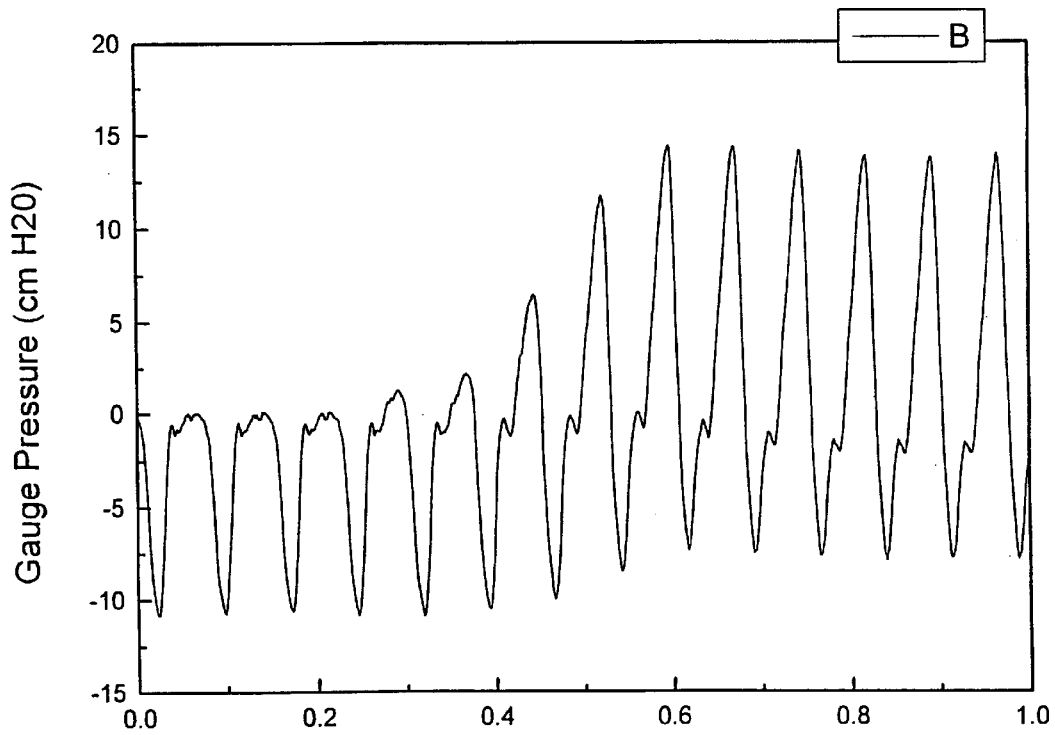
FIG. 23 shows a graph of a sample pressure plot with clogged normalizing valve indicating baseline drift.

The need for the normalizing valve is further witnessed in FIG. 23, which reveals the baseline drift as predicted in the theoretical simulations. At 0.4 sec, the valve was plugged and the resultant steady shift in the baseline can be seen. After 0.3 sec, a new equilibrium is reached. This small time constant indicates that there are other sources of leakage in the system apart from the modeled gap. Furthermore, as the valve is plugged, the amplitude of the pressure swing increases, showing that the valve is one such source.

Figure 24:
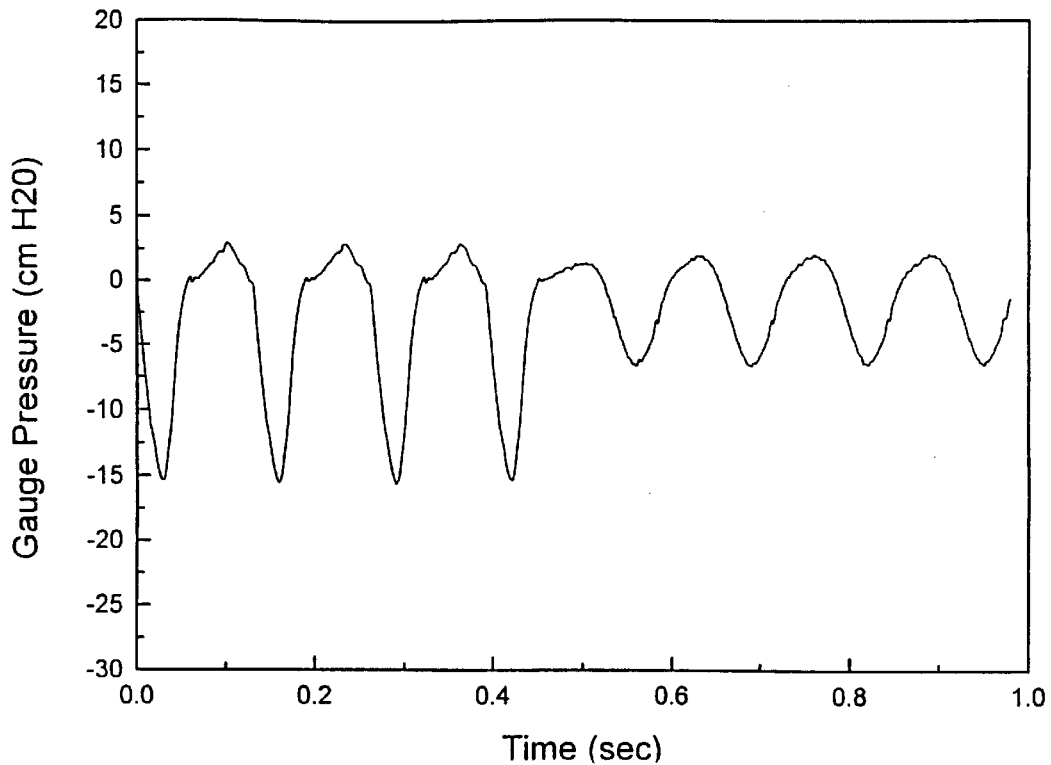
FIG. 24 shows a graph of a pressure profile fluctuation with dead space change.

The function of the 20 ml dead space can be seen in FIG. 24. The connection to the 20 ml dead space was clamped until 0.7 sec. At this point, the line was open and the resulting drop in pressure can be seen. Under the given conditions, the pressure is nearly halved. As discussed, this mechanism can be used in pressure calibrations and adjustments while the ventilator is in operation.

Overall, the mechanical performance of the ventilator is adequate. The pressures can be varied over a wide frequency range allowing both for normal and high frequency modes of ventilation. Though proper function is not achievable at frequencies much greater than 50 Hz with the current spring, this drawback allows a significant amount of power to be saved. However, if frequencies much higher than 50 Hz are desired, the spring can accordingly be changed.

Figure 25:
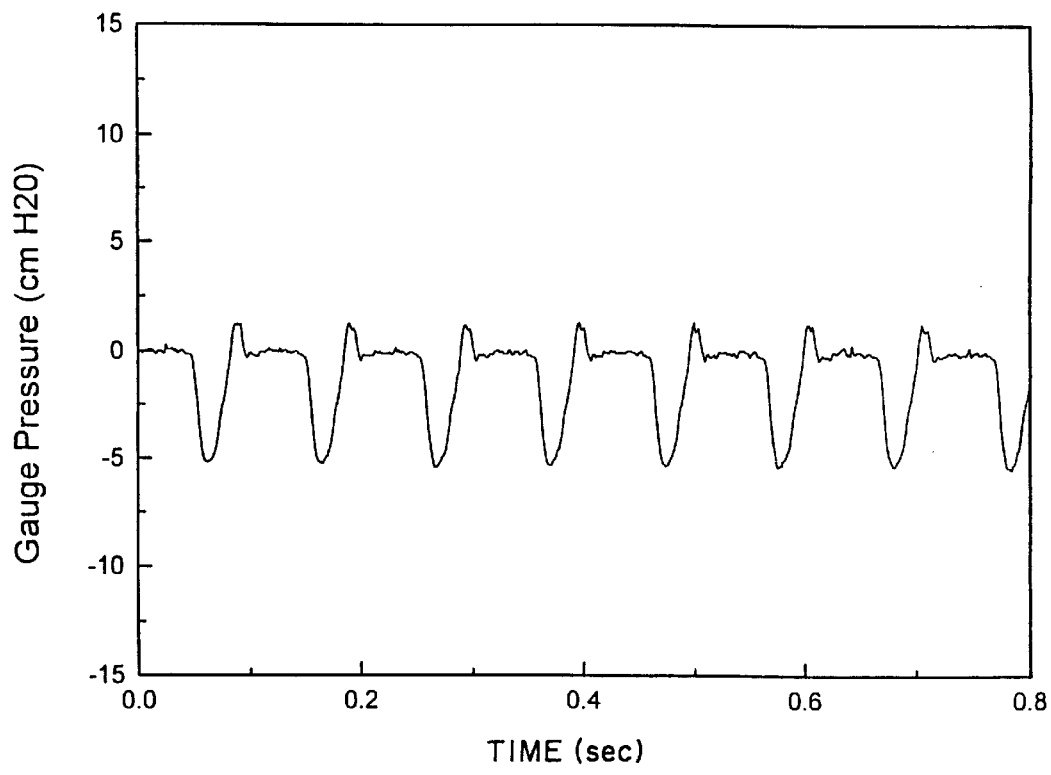
FIG. 25 shows a graph of a pressure profile of typical in-vivo recording (10 Hz, 5 cm $H_2O$)

Actual ventilator testing has been performed on both normal control and mutant mice. The primary use of the controls was to ensure that the ventilator was not harming the mice. FIG. 25 shows a sample recording on a newborn mouse (10 Hz/ 5 cm $H_2O$). The preliminary goal of these tests was to ascertain if the ventilator could prolong the lives of the mutants. As expected, the control mice lived regardless of ventilatory assistance.

Figure 26:
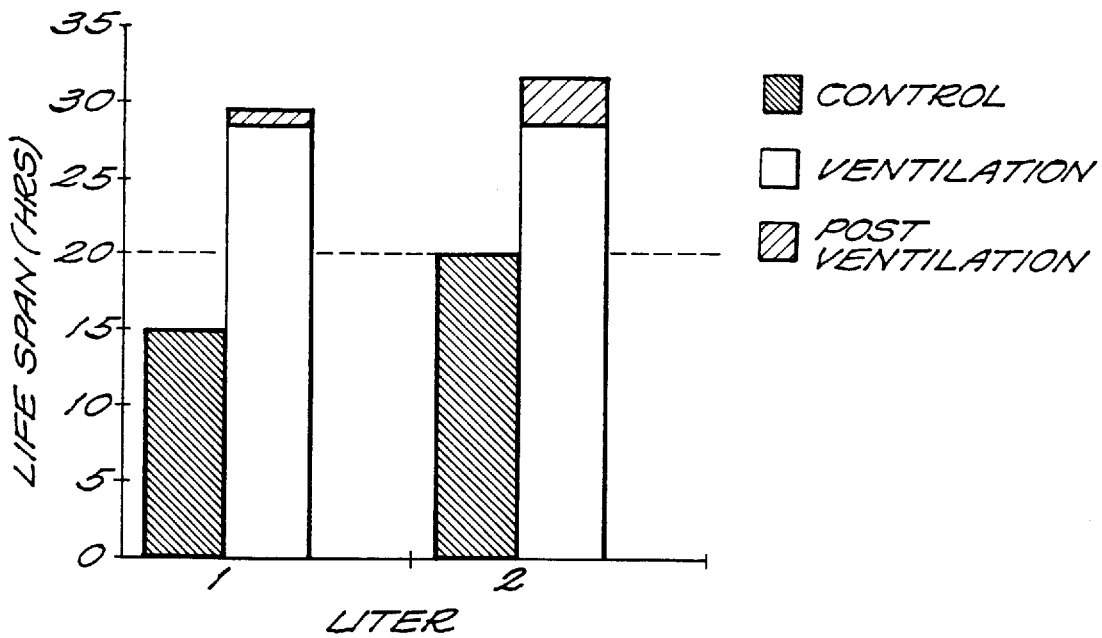
FIG. 26 shows a graph of life span of mutants and control littermates.

Two liters containing mutants were tested on the ventilator. In each trail, one mutant was placed in the device and the remainder mutant liter mates were used as controls. Frequencies between 10 and 20 Hz were used with pressure swings of around 6 cm $H_2O$ for these trials. FIG. 26 compares the life spans of the respirated and non-respirated mice. The total span is divided into time on the ventilator and time after being taken off. Also, the maximum life span (20 hrs) of unventilated mice is given as a limit on the graph.

FIG. 26 clearly shows that the life span of the mutants seems to be prolonged with respiratory aid. In both instances, the ventilated mice outlived their liter mate controls, and furthermore, broke the previous life span boundary set at 20 hours.

A possible explanation for the eventual death of the ventilated mice is starvation. As mentioned before, the mutants have several abnormalities, including an inability to suckle milk. Therefore, they are not feed from the time of birth and are severely malnourished (even normal mice cannot survive long without food).

The short post-ventilator life of the first mutant, also indicates that the ventilator may train the mice to cease spontaneous breathing. Apparently, after being taken off the ventilator, the mutant did not re-start the process and died. Ventilator training is a major concern in human respiration. After being on a ventilator for a prolonged period of time, patients must undergo a weaning process in order to resume self-initiated breathing. If this is indeed the case, a similar strategy may have to be adopted for the mice.

One question that remains to be answered is whether the respiratory failure is caused by systemic malfunction or CNS command errors as predicted by faulty NMDA receptors. Currently, lung pathology experiments are being performed on the mutant mice to see if the lungs can be preserved through ventilation, thereby indicating a CNS malfunction.

Regardless, many more tests must be performed to fully understand the proper techniques and role of mechanical ventilation in the neonatal mice.

The need for a mechanical ventilator for newborn mice has arisen from NMDA knockout mice. This genetic alteration affects the mice in various ways including respiratory distress. The malfunction is believed to result in respiratory failure leading to the premature death of the newborn animals, thereby impeding further investigative efforts into the role of the NMDA receptors in neural development.

Ventilatory assist was chosen as a means of foregoing respiratory failure in hopes of sustaining the mutant mice. Previous ventilator designs do not allow for respiratory aid on such a small scale. Therefore, a high frequency negative pressure ventilator was designed.

The ventilator is unique in several ways. Since the device can achieve wide spectrum of pressure fluctuations over a large frequency range, it is effective in both normal and high-frequency ventilation. This variability is needed since newborns of this nature have never been ventilated before, and the proper techniques are not known. Additionally, the double piston design (pressure piston and valve piston), elegantly normalizes the chamber pressure, allowing negative pressures to be generated efficiently. The valve mechanism also keeps positive pressures from building around the body surface, which would be detrimental to respiratory efforts.

Preliminary studies have indicated that the life span of the ventilated mutant mice can be prolonged by around 10 hrs. Still, many more studies must be performed to ascertain the proper ventilatory parameters for such newborn mice, and the exact effects of ventilation.

As seen in the description of performance above, the valve is non-functional at extremely high frequencies. In future designs, the spring constant can be varied to the full 3950 N/m to allow valve synchronization at 100 Hz. An alternative method to achieve similar results, yet minimize power consumption, is to reduce the weight of the cam shaft. However, before either option is fully considered, the effective ventilation range for the newborn mice should be determined.

Also, the current method of negative pressure ventilation requires that a cuff be place around the neck of the newborn animal. Although this technique is much less invasive than a tracheotomy, it still has the risk of closing the subjects airway's, increasing the resistance to flow. Another option is to place the cuff around the body, and simply oscillate the mouse's abdomen. Previous studies have shown this to be an extremely effective method of negative pressure ventilation.

Another future consideration is temperature control over the mouse chamber. Currently, unventilated mice are kept in an incubator since their homeostatic mechanisms are not adequate at such a young age. However, the present design does not account for this problem.

Furthermore, as mentioned in the pressure generating piston section, positive pressures serve to close the airways, where as negative pressures open them. Therefore, a negative pressure source connected to the outlet of the normalizing valve would create a negative end expiatory pressure, helping to open the airways. This strategy has been employed in modern positive pressure ventilators (positive end expiatory pressure) and helps to negate the effects of airway resistance.

The miniature HF ventilator discussed herein is an excellent stepping stone in the respiration of incapable newborn mice. Various changes could further the effectiveness of any such attempts. Regardless, the use of the ventilator has been shown to increase the life spans of tested mutant mice, and additional studies are currently being performed to support these initial findings.

Additional design features of the ventilator of the present invention are set forth as follows.

Figure 27:
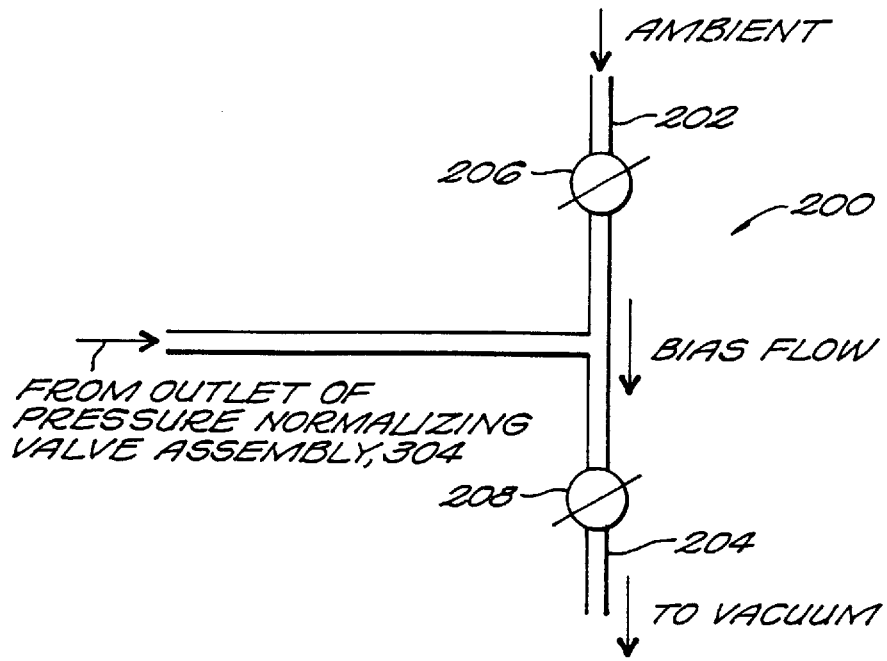
FIG. 27 is a schematic block diaghram of a bias flow system.

The "atmospheric intake" in FIG. 3 is normally open to ambient atmosphere. Alternatively, it may be open to some bias negative pressure to provide negative end-expiratory pressure (NEEP) to help inflate the lungs at the end of expiration. One way to do so is to connect the outlet of the pressure normalizing valve assembly 304 (FIGS. 9A and 9B) to a bias flow system 200 as shown in FIG. 27. The bias flow system includes, for example, an inlet 202 connected to ambient atmospheric conditions, an outlet 204 connected to a vacuum source, and two control valves 206,208 connected between the inlet and outlet.

The idea of NEEP is similar to the idea of positive end-expiratory pressure (PEEP) commonly found in positive pressure ventilators which are widely used in hospitals.

Figure 28:
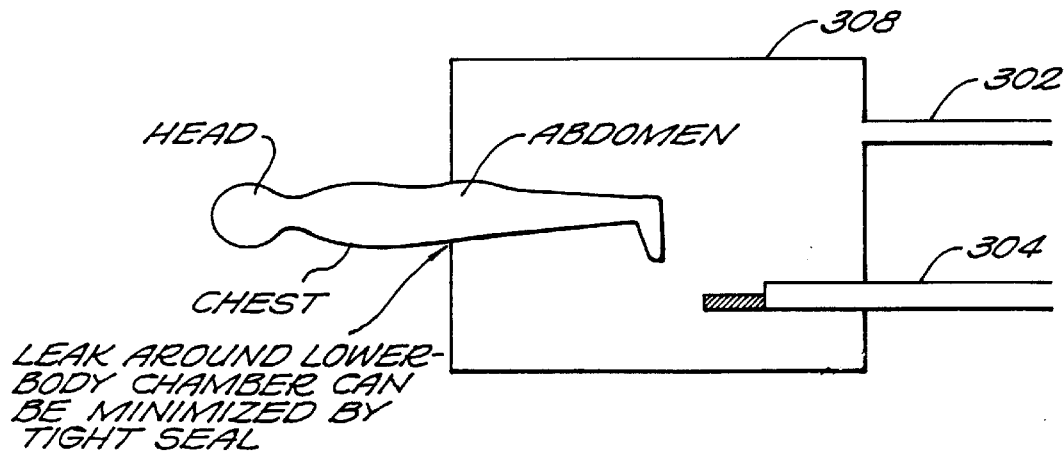
FIG. 28 is a block diaghram of a chamber enclosing the lower body of a patient.

In the present invention, the animal or patient is placed in a head-out position and negative oscillatory pressure is applied to the chest and lower body. Alternatively, one can move the animal/patient outward so that the chamber only encloses the lower body (below the diaphragm) and negative pressure oscillation is applied only to the abdomen and lower body as shown in FIG. 28. In this configuration, the chamber can be sealed even tighter around the body trunk which is not as much at risk of choking as is sealing around the neck region. Lower-body oscillation has been proposed before in a prior publication but not in the present setting.

Figure 29:
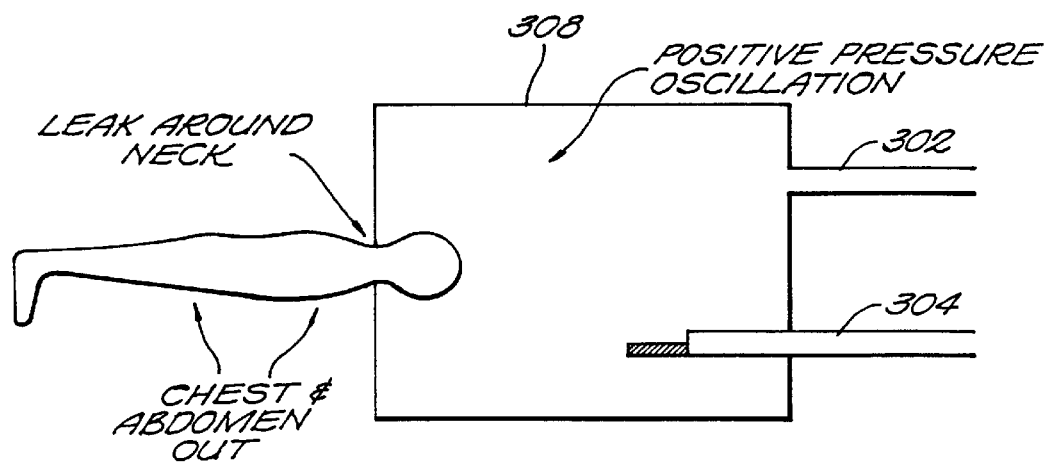
FIG. 29 is a block diaghram of a chamber enclosing the head of a patient.

In some situations, it maybe advantageous to reverse the body chamber position so that the head of the animal/patient is enclosed in a head chamber (hood) where positive (instead of negative) oscillatory pressure is applied to ventilate the lungs and a bias flow is used to replenish the air and anesthetic gas/aerosols as shown in FIG. 29. This may free up the subject's lower body for surgical operation, intravenous fluid/drug administration or other body care.

Furthermore, optional incubation chamber can be added to the ventilator to enclose the animal/patient and body chamber. This is necessary for babies or newborn animals who usually cannot regulate their body temperature.

The foregoing description has been set forth to illustrate the invention and is not intended to be limiting. Since modifications of the described embodiments incorporating the spirit and substance of the invention may occur to persons skilled in the art, the scope of the invention should be limited solely with reference to the appended claims and equivalents thereof.

---

Appendix A: Respiratory Mechanics Model (qbasic)

```
vdes=.04
tol=.001
Phigh=40
plow=O
screen 2, 1
REM parameters
po=(phigh+plow)/2
w=1
dt=.01/w
w=w*2*3. 1415
REM Constants
r=2.314
e=554
tme=1
start:
        LOCATE 1,1:PRINT po, vhigh
        REM Initial Conditions
        vo=0
        vhigh=0
        FORt=0 TO tme STEP dt
            p=-po/2*COS(w*t)+po/2
            v=(p-r*ABS(f))le
            f=(v-vo)/dt
            vo=v
            IF v>vhigh THEN vhigh=v
```

-continued

Appendix A: Respiratory Mechanics Model (qbasic)

```
        NEXT t
        IF (vhigh-vdes)>tol THEN
                phigh=po
                po=(phigh+plow)/2
        ELSE
                plow=po
                po=(phigh+plow)/2
        ENDIF
GOTO start
```

Appendix B: Piston Model (MATLAB)

```
function dy=model(t,y)
m=y(1);                         mass
p=y(2);                         pressure
x=y(3);                         position
;PARAMETERS
r1=.00245;                      shaft radius
r2=.00255;                      cylinder radius
l=.05;                          normal gap length
vmin=15e-6;                     minimal chamber volume
x6=.03                          stroke length
;CONSTANTS
R=287;                          gas constant (air)
k=298;                          ternperature
u=1.82e-5;                      viscosity (air)
b=1.204;                        density (air)
pa=1e5;                         atmospheric pressure
xmax=.03;                       max stroke length
a=pi*r1^2;                      piston area
h=r2-r1;                        gap
vc=((xmax-xo)/2)*pi*r2^2+vmin;  extra pisotn volume
;DIFFERENTIAL RELATIONS
dx=w*xo/2* sin(w*t);
dm=2*b*pi*r1*((dx*h/2)-(h^3)*(p-pa)/(12*u*(xo)+1-x)));
dp=(dm*R*k-a*p*dx)/(a(*x+vc);
dy(1)=dm;
dy(2)=dp;
dy(3)=dx;
```

What is claimed is:

1. A pressure ventilator system, comprising:
   a pressure chamber arranged to surround a portion of a patient's thoracic cavity so as to isolate a portion of a patient's body from atmospheric pressure;
   a pressure modulator operable for modulating the pressure within said chamber and cyclically applying negative external pressure to said portion of the body during a negative cycle of operation; and
   a pressure normalizer operable during a positive cycle of operation for normalizing a base pressure about which the pressure within said chamber is modulated, said pressure normalizer comprising an assembly which cyclically opens a valve arrangement within said chamber to expose said chamber to a predetermined pressure.

2. The system of claim 1, wherein said chamber comprises a variable volume pressure chamber operating in the range of about 5 to 25 ml/breath.

3. The system of claim 1, wherein said system produces tidal volumes ranging between about 0 to 0.045 ml.

4. The system of claim 1, wherein the amplitude of the pressure within said chamber is varied between about 0 to 25 cm $H_2O$.

5. The system of claim 1, wherein said pressure modulator operates in a frequency range between about 0 to 100 Hz.

6. The system of claim 1, wherein said pressure modulator comprises a reciprocating piston pump assembly which oscillates the pressure within said chamber.

7. The system of claim 1, wherein said assembly of said pressure normalizer comprises a cam-driven piston assembly which cyclically opens said valve arrangement within said chamber to expose said chamber to a predetermined pressure.

8. The system of claim 7, wherein said predetermined pressure is atmospheric pressure.

9. The system of claim 7, wherein said predetermined pressure is a pressure biased above or below atmospheric pressure.

10. A high-frequency pressure ventilator system, comprising:
    a variable volume pressure chamber arranged to surround a portion of a patient's thoracic cavity so as to isolate a portion of a patient's body from atmospheric pressure;
    a pump assembly operable for varying the pressure within said chamber so as to apply negative external pressure to said portion of the body during a negative cycle of operation; and
    a valve assembly operable for opening said chamber to a predetermined pressure during a positive cycle of operation in order to normalize a base pressure from which the pressure within said chamber is varied, said valve assembly comprising a module which cyclically opens a valve arrangement within said chamber to expose said chamber to said predetermined pressure.

11. The system of claim 10, wherein said chamber operates in the range of about 5 to 25 ml/breath.

12. The system of claim 10, wherein said system produces tidal volumes ranging between about 0.015 to 0.045 ml.

13. The system of claim 10, wherein the amplitude of the pressure within said chamber is varied between about 0 to 25 cm $H_2O$.

14. The system of claim 10, wherein said pump assembly operates in a frequency range between about 1 to 100 Hz.

15. The system of claim 10, wherein said valve assembly modulator comprises a reciprocating piston pump which oscillates the pressure within said chamber.

16. The system of claim 10, wherein said module of valve assembly comprises a cam-driven piston which cyclically opens a valve arrangement within said chamber to expose said chamber to a predetermined pressure.

17. The system of claim 16, wherein said predetermined pressure is atmospheric pressure.

18. The system of claim 16, wherein said predetermined pressure is a pressure biased above or below atmospheric pressure.

19. A method of applying external negative pressure to a thoracic cavity of a body, comprising:
    surrounding a portion of the thoracic cavity of said body within a pressure chamber so as to isolate the portion from atmospheric pressure;
    varying the pressure within said chamber so as to apply negative external pressure to said portion of the body during a negative cycle of operation; and
    opening said chamber with a valve assembly to a predetermined pressure during a positive cycle of operation in order to normalize a base pressure from which the pressure within said chamber is varied, said valve assembly including a module which cyclically opens a valve arrangement within said chamber to expose said chamber to said predetermined pressure.

20. A pressure ventilator system, comprising:
    a pressure chamber arranged to surround a patient's head so as to isolate said head from atmospheric pressure;

a pressure modulator operable for modulating the pressure within said chamber and cyclically applying positive external pressure to a patient's head during a positive cycle of operation; and a pressure normalizer operable during a negative cycle of operation for normalizing a base pressure about which the pressure within said chamber is modulated, said pressure normalizer comprising an assembly which cyclically opens a valve arrangement within said chamber to expose said chamber to a predetermined pressure.

21. A high-frequency pressure ventilator system, comprising:

a variable volume pressure chamber arranged to surround a patient's head so as to isolate said head from atmospheric pressure;

a pump assembly operable for varying the pressure within said chamber so as to apply positive external pressure to a patient's head during a positive cycle of operation; and a valve assembly operable for opening said chamber to a predetermined pressure during a negative cycle of operation in order to normalize a base pressure from which the pressure within said chamber is varied, said valve assembly comprising a module which cyclically opens a valve arrangement within said chamber to expose said chamber to said predetermined pressure.

22. A method of applying external positive pressure to a portion of a body, comprising:

surrounding the portion of the body within a pressure chamber so as to isolate said portion from atmospheric pressure;

varying the pressure within said chamber so as to apply positive external pressure to the portion of the body during a positive cycle of operation; and opening said chamber with a valve assembly to a predetermined pressure during a negative cycle of operation in order to normalize a base pressure from which the pressure within said chamber is varied, said valve assembly including a module which cyclically opens a valve arrangement within said chamber to expose said chamber to said predetermined pressure.

* * * * *